(12) United States Patent
Zhi et al.

(10) Patent No.: US 7,662,804 B2
(45) Date of Patent: Feb. 16, 2010

(54) THROMBOPOIETIN ACTIVITY MODULATING COMPOUNDS AND METHODS

(75) Inventors: Lin Zhi, San Diego, CA (US); E. Adam Kallel, Escondido, CA (US); Dean P. Phillips, San Marcos, CA (US)

(73) Assignee: SmithKline Beecham Corp., Philadelphia, PA (US)

( * ) Notice: Subject to any disclaimer, the term of this patent is extended or adjusted under 35 U.S.C. 154(b) by 206 days.

(21) Appl. No.: 11/562,327

(22) Filed: Nov. 21, 2006

(65) Prior Publication Data

US 2007/0129539 A1 Jun. 7, 2007

Related U.S. Application Data

(63) Continuation of application No. PCT/US2005/18924, filed on May 27, 2005.

(60) Provisional application No. 60/575,196, filed on May 28, 2004.

(51) Int. Cl.
| C07D 403/12 | (2006.01) |
| C07D 231/46 | (2006.01) |
| A61K 31/655 | (2006.01) |
| A61K 31/41 | (2006.01) |
| A61K 31/4152 | (2006.01) |
| A61P 7/00 | (2006.01) |

(52) U.S. Cl. .................. 514/150; 514/381; 514/404; 534/775; 534/792; 548/253; 548/367.4

(58) Field of Classification Search ............... None
See application file for complete search history.

(56) References Cited

U.S. PATENT DOCUMENTS

| 1,792,355 | A | 2/1931 | Boeniger |
| 3,150,151 | A | 9/1964 | Urbschaft et al. |
| 3,208,991 | A | 9/1965 | Blout et al. |
| 3,718,678 | A | 2/1973 | Farrand et al. |
| 3,754,857 | A | 8/1973 | McKay |
| 3,966,900 | A | 6/1976 | Hennart et al. |
| 4,322,533 | A | 3/1982 | Lesher et al. |
| 4,451,398 | A | 5/1984 | Patsch et al. |
| 4,720,304 | A | 1/1988 | Ruff et al. |
| 5,001,229 | A | 3/1991 | Franke et al. |
| 5,051,417 | A | 9/1991 | Nadler et al. |
| 5,155,015 | A | 10/1992 | Jimbo |
| 5,164,404 | A | 11/1992 | Dahl et al. |
| 5,298,658 | A | 3/1994 | Fabricius |
| 5,482,546 | A | 1/1996 | Eida |
| 5,766,581 | A | 6/1998 | Bartley et al. |
| 6,075,044 | A | 6/2000 | Wang et al. |
| 6,448,238 | B1 | 9/2002 | Shoichet et al. |
| 6,552,008 | B1 | 4/2003 | Duffy et al. |
| 6,642,265 | B1 | 11/2003 | Luengo et al. |
| 6,649,631 | B1 | 11/2003 | Orme et al. |
| 6,670,387 | B1 | 12/2003 | Luengo et al. |
| 6,720,345 | B1 | 4/2004 | Luengo et al. |
| 6,875,786 | B2 | 4/2005 | Duffy et al. |
| 6,916,798 | B2 * | 7/2005 | Green et al. ................. 514/150 |
| 6,964,701 | B2 | 11/2005 | Foster et al. |
| 6,964,977 | B2 | 11/2005 | Harris et al. |
| 7,026,334 | B1 | 4/2006 | Takemoto et al. |
| 7,071,217 | B2 | 7/2006 | Dickerson et al. |
| 7,105,529 | B2 | 9/2006 | Davis et al. |
| 7,129,253 | B2 | 10/2006 | Glennon et al. |
| 7,135,550 | B2 | 11/2006 | Come |
| 7,160,870 | B2 | 1/2007 | Duffy et al. |
| 7,335,649 | B2 * | 2/2008 | Duffy et al. .................. 514/150 |
| 7,414,040 | B2 * | 8/2008 | Heerding ..................... 514/150 |
| 2003/0229453 | A1 | 12/2003 | Antonysamy et al. |
| 2004/0019190 | A1 | 1/2004 | Erickson-Miller et al. |
| 2004/0053299 | A1 | 3/2004 | Delorme et al. |
| 2004/0058990 | A1 | 3/2004 | Duffy et al. |
| 2004/0082626 | A1 | 4/2004 | Takemoto et al. |
| 2004/0220146 | A1 | 11/2004 | Freeman et al. |
| 2004/0253178 | A1 | 12/2004 | Atwell et al. |
| 2005/0049267 | A1 | 3/2005 | Suto et al. |
| 2005/0153977 | A1 | 7/2005 | Sugasawa et al. |
| 2005/0234020 | A1 | 10/2005 | Heerding |
| 2006/0069140 | A1 | 3/2006 | Miyaji et al. |
| 2006/0084682 | A1 | 4/2006 | Heerding et al. |
| 2006/0094694 | A1 | 5/2006 | Owada et al. |
| 2006/0116417 | A1 | 6/2006 | Chen et al. |

(Continued)

FOREIGN PATENT DOCUMENTS

BE 653800 3/1965

(Continued)

OTHER PUBLICATIONS

Lipinski, "Bioisosteres in Drug Design", Annual Reports in Medicinal Chemistry, 21, 283-291, 1986.*
Snavely et al., Chemical Abstraccts, 58:6914, 1963 (Registry No. 98439-02-2).*
Snavely et al., Inorganic Chemistry, 1(4), 890-892, 1963.*
Abdel-Latif et al., "Reaction of Diazocompounds and Hydrazines on Indolin-2-one Derivatives", *Indian J. Chem.*, 1985, 24B(7), 775-777.
Abdel-Rahman et al., "Synthesis of some 1,2,4-Triazino [4,3-a] indole derivatives", *J. Indian Chem. Soc.*, 1991, 68(11), 621-624.
Abdel-Rahman et al., "Synthesis of Some New 2,3/2,4-Disubstituted-1,2,4-Trianzino [5,6-b] Indoles", *Asian J. Chem.*, 1992, 4(2), 364-371.

(Continued)

*Primary Examiner*—Fiona T Powers
(74) *Attorney, Agent, or Firm*—Wayne J. Dustman; Edward R. Gimmi; Charles M. Kinzig

(57) ABSTRACT

Disclosed herein are novel diazenyl pyrazole compounds and related compounds. Also disclosed herein are methods of using these compounds for the treatment of diseases and conditions associated with modulating a thrombopoietin activity.

7 Claims, No Drawings

U.S. PATENT DOCUMENTS

| | | | |
|---|---|---|---|
| 2006/0178518 | A1 | 8/2006 | Moore |
| 2007/0105824 | A1 | 5/2007 | Erickson-Miller et al. |

FOREIGN PATENT DOCUMENTS

| | | | |
|---|---|---|---|
| DE | 193633 | | 2/1907 |
| DE | 450819 | | 10/1927 |
| DE | 4335623 | | 4/1995 |
| EP | 0141067 | | 8/1984 |
| EP | 0335237 | | 3/1989 |
| GB | 1080864 | | 8/1967 |
| GB | 2 168 347 | A | 6/1986 |
| JP | 2-287457 | | 11/1990 |
| JP | 2000-206645 | | 7/2000 |
| JP | 2001-152055 | | 5/2001 |
| JP | 2002-020641 | | 1/2002 |
| JP | 2002-129072 | | 5/2002 |
| JP | 2002-129073 | | 5/2002 |
| JP | 2003-128946 | | 5/2003 |
| JP | 2003-313450 | | 11/2003 |
| JP | 2003-335972 | | 11/2003 |
| JP | 2004-143118 | | 5/2004 |
| WO | WO 01/17349 | | 3/2001 |
| WO | WO 01/21180 | A1 | 3/2001 |
| WO | WO 01/89457 | | 11/2001 |
| WO | WO 03/011287 | * | 2/2003 |
| WO | WO 03/037905 | A1 | 5/2003 |
| WO | WO 03/082265 | A2 | 9/2003 |
| WO | WO 03/098992 | | 12/2003 |
| WO | WO 03/103686 | | 12/2003 |
| WO | WO 2005/097119 | A2 | 10/2005 |
| WO | WO 2005/107466 | A1 | 11/2005 |
| WO | WO 2005/118551 | | 12/2005 |
| WO | WO 2006/004545 | | 1/2006 |
| WO | WO 2006/052936 | A2 | 5/2006 |
| WO | WO 2006/076442 | | 7/2006 |
| WO | PCT/US2007/006547 | | 3/2007 |
| WO | WO 2007/062078 | | 5/2007 |

OTHER PUBLICATIONS

Alam et al., "Analytical studies of biologically active compounds-I: Quantitative Determination of Metabolies of 3-Substituted Isatin Derivatives by TLC", *Proc. Pakistan Acad. Sci.*, 1992, 29(2), 113-120.

Alam et al., "Biopharmaceutical Studies of 3-Substituted Isatin Derivatives", *Indian J. Exp. Biol.*, 1990, 28(10), 940-942.

Alam et al.,"Electronic Spectra of Isatin Derivatives", *Proc. Pakistan Acad. Sci.*, 1987, 24(4), 337-348.

Ali, et al., "Analytical Studies on Biologically Active Compounds. Part II. Separation and Quantitation of Mixtures of Isatin Derivatives for Application to Metabolism Studies", *Pak. J. Sci. Ind. Res.*, 1995, 38(8), 330-332.

Aly, et al., "Reaction of 1-Acetyl-3-dicyanomethylene-1,3-dihydro-2H-indol-2-one with Some Nucleophilic Reagents: Synthesis of Some Indole and Quinoline Derivatives", *Heterocyclic Comm.*, 2000, 6(3), 249-252.

Aly, et al., "Synthesis and reactions of 1,3-dihydro-3-(3',5'-dioxo-2'H-1'-phenylpyrazolidene) -2h-indol-2-one", *Bull. Fac. Sci., Assuit Univ.*, 1996, 25(1-B), 25-33.

Amin, "Spectrophotometric Method for the Determination of Titanium in Soil, Geo—Chemical, Silicates Rock and Paint Samples", *Quim. Anal.*, 2002, 20, 217-222.

Amin, et al., "Simultaneous Spectrophotometric Determination of Thorium and Rare Earth Metals with Pyrimidine Azo Dyes and Cetylpyridinium Chloride", *Talanta*, 2001, 54(4), 611-620.

Atta et al., "β-Lactam Formation on Thin-Layer Chromatoplates", *Indian J. Chem.*, 1979, 18B(5), 475-476.

Back et al., "Zusammenhange zwischen Konstitution von neutralziehenden Metallkomplexfarbstoffen, Verteilungsgleichgewichten zwischen flussigen Phasen und Farbegleichgewichten auf Polyamiden", *Helv. Chim. Acta*, 1959, 166, 1539-1553.

Bains et al. "Silicon chemistry as a novel source of chemical diversity in drug design." *Current Opinion in Drug Discovery and Development*; 6(4):526-543 (2003).

Ballantine et al., "Rearrangement and Cyclization in the Mass Spectra of a Series of Isatin Carbonyl Derivatives of Medicinal Interest. 2-Oxo-3-Indolinylidene Anils (N-Arylketimines), 2-Oxo-3-Indolinylidene Phenylhydrazones, 2-Oxo-3, 3-Bis (*O*-Diaminoaryl) Indolyl Derivatives and Their 2,3- Quinoxaline Heterocyclic Analogues", *Organic Mass Spectrometry*, 1971, 5(8), 1003-1014.

Bartley et al. "Identification and Cloning of a Megakaryocyte Growth and Development Factor That Is a Ligand for the Cytokine Receptor Mpl." *Cell*; 77:1117-11124 (1994).

Baser et al., 1997, *Blood*, 89,3118-3128.

Bauer, "Oxalic Acid Quinochlorides (II)", *Berichte der Deutschen Chemischen Gesellschaft*, 1909, 42, 2111-2118.

Bauer, "Uber Oxalsaure-imidchloride", *Berichte der Deutschen Chemischen Gesellschaft*, 1907, 2650-2663.

Beaton, et al., "Preparation and Hydrogen Bonding Studies of Phenylhydrazone Derivatives Of Alloxan: Crystal And Molecular Structure of Pyrimidine-2(1*H*),4(3*H*),5,6-tetraone 5-(2-nitrophenyl) hydrazone", *J. Chem. Soc., Perkin Trans. II*, 1987, (4), 469-472.

Bogert et al., "Azo Derivatives of the Pyrimidines", *Proc. Natl. Acad. Sci.*, 1932, 18,215-222.

Bramson, et al., Oxindole-Based Inhibitors of Cyclin-Dependent Kinase 2 (CDK2): Design, Synthesis, Enzymatic Activities, and X-ray Crystallographic Analysis, *J. Med. Chem.*, 2001, 44(25), 4339-4358.

Braun et al., "Isatin-4-Carbonsäure", *Berichte der Deutschen Chemischen Gesellschaft*, 1923, 2343-2347.

Buu-Hoi et al, "Carcinogenic Nitrogen Compounds. XIII. Benzacridines, benzacarbazoles, and Related Compounds Bearing Ethyl and Propyl Groups", *J. Chem. Soc.*, 1952, 4867-4869.

Buu-Hoi; et al,, "On New Isatines", *Bull. Soc. Chim. Fr.*, 1946, 586-587.

Cedere et al., "Reversible Inhibitors of Monomine Oxidase in the Indolinone Series", *Khimiki-Farmatsevticheskii Zhumal*, 1984, 18(5), 555-558.

Chan et al., "Barbituarate analogs of salazosulfanilamides", Khimiko-Farmatsevticheskii Zhurnal, 1973, 7(4), 26-30.

Chuaqui, et al., "Interaction Profiles of Protein Kinase-Inhibitor Complexes and Their Application to Virtual Screening", *J. Med. Chem.*, 2005, 48(1), 121-133.

Coda et al., "The Copper (II) Acetate Complex of Isatin 3-Phenylhydrazones: An Unusual Role of Arylhydrazones as Ligands", *Gazz. Chim. Ital.*, 1985, 115(10), 549-553.

Congreve, et al., "Detection of Ligands From a Dynamic Combinatorial Library by X-ray Crystallography", *Angew. Chem., Int. Ed. Engl.*, 2003, 42(37), 4479-4482.

Corsico Coda et al., "Copper (II) in Organic Synthesis. IV[1] Reaction of the Copper (II) Acetate Complex of Isatin-3-arylhydrazones with Dimethyl Acetylenedicarboxylate", *Tetrahedron*, 1985, 41(12), 2545-2555.

Costopanagiotis et al., "Application of Mass Spectrometry to the Analyses of Pharmaceuticals. Mass Spectra of Barbituric Acid Derivatives", *Mh. Chem.*, 1965, 96(6), 1800-1808.

Crippa et al., "Imesatins. II. New Developments and Clarification of Mayer's Synthesis", *Gazz. Chim. Ital.*, 1951, 81, 195-204.

Cwirla et al. "Peptide Agonist of the Thrombopoietin Receptor as Potent as the Natural Cytokine". *Science*; 276:1696-1699 (1997).

Da Settimo et al., "Reactions of 2, 3-Dibromoindole Derivatives with Bromine and Other Oxidizing Agents", *J. Org. Chem.*, 1974, 39(14), 1995-1998.

Database Beilstein. Beilstein Institute for Organic Chemistry, Frankfurt-Main, DE; XP-002364395. Database accession No. BRN: 1499659; BRN: 1554046; BRN: 1554047.

Database Beilstein. Beilstein Institute for Organic Chemistry, Frankfurt-Main, DE; XP-002364396. Database accession No. BRN: 1513709.

Database Caplus Chemical Abstracts Service, Columbus, Ohio, US; XP-002364397 retrieved from STN accession No. 1978: 443178 Database accession No. 89: 43178.

De Sauvage et al., *Nature*, 1994, 369, 533-538.

Delimoge et al., "Simple Synthetic Routes to 5-(3,6-dihydro-2-oxo-2H-1,3,4-thiadiazin-5-yl)-1H indole-2,3-diones and their derivatives", *J. Heterocycl. Chem* 1991, 28(6), 1525-1532.

Dessouki et al., Structural Investigation of Isatinβ -Arylhydrazone Derivatives by UV, IR, $^1$H NMR Spectra and PPP CI Calculations, *Spectrochimica Acta*, 1988, 44A(8), 849-851.

Di Carlo et al., "Synthesis and Properties of 1-Cyanoethylisatin", *J. Am. Chem. Soc.* 1945, 67, 199-201.

Dobrynin et al., "Relationship Between the Structure and the Cytotoxic Action of 3-Deriviatives of 1-Glycosylisatins", *Pharm. Chem. J.*, 1984, 18(12), 807-810.

Duffy et al. "Hydrazinonaphthalene and Azonaphthalene Thrombopoietin Mimics are Nonpeptidyl Promoters of Megakaryocytopoiesis." *J. Med. Chem.*, 2001, 44, 3730-3745.

Duffy et al. "Identification of a Pharmacophore for Thrombopoietic Activity of Small Nonpeptidyl Molecules. 1. Discovery and Optimization of Salicylaldehyde Thiosemicarbazone Thrombopoietin Mimics." *J. Med. Chem*, 2002, 45, 3573-3575.

Duffy et al. "Identification of a Pharmacophore for Thrombopoietic Activity of Small Nonpeptidyl Molecules. 2. Rational Design of Naphtha[1,2-d]imidazole Thrombopoietin Mimics." *J. Med. Chem*, 2002, 45, 3576-3578.

Dureja, et al., "Topochemical Models for Prediction of Cyclin-Dependent Kinase 2 Inhibitory Activity of Indole-2-ones", *J. Mol. Model.*, 2005, 11(6), 525-531.

Efremenko et al., "Azo-Coupling of 2,6-Di-tert-butyl-p-benzoquinone diazide with β-Dicarbonyl Compounds", *Bull. Acad. Sci. USSR Div. Chem. Sci.* (Engl. Transl.), 1971, 20, 2711-2712.

El Ashry et al., "Ring Expansion of Indoline-2,3-dione-3-phenylhydrazone to 3,1-Benzoxazine-2, 4(1H)-dione-4-phenylhydrazone", *Indian J. Chem*, 1978, 16B(11), 1036-1038.

Elguero et al, "Recherches dans la Serie des Azoles. XII.— Structure des Phenylazo-4 Pyrazolones-5", *Bull. Soc. Chim. Fr.*, 1966, 2990-2995.

Elguero et al., "The Tautomerism of Heterocycles", *Adv. Heterocycl. Chem. Spl. 1*, 321-339, Katritzky and Boulton eds., Academic Press, 1976, New York.

Ei-Shafei, et al., "Semi-Empirical Molecular Orbital Methods in the Design of Organic Colorants", *AATCC Review*, 2001, 23-26.

Erickson-Miller et al. "Discovery and characterization of a selective, nonpeptidyl thrombopoietin receptor agonist." *Experimental Hematology*, 2005, 33, 85-93.

Fadda, et al., "Synthesis of azodisperse dyes with pyridine ring for dyeing polyester fibres: Part II", *Indian Journal of Textile Research*, 1989, 14, 177-183.

Fanucchi et al., 1997, *New Engl. J. Med.*, 336, 404-409.

Feher, et al., BHB: A Simple Knowledge-Based Scoring Function to Improve the Efficiency of Database Screening *J. Chem. Int Comput. Sci.*, 2003, 43(4), 1316-1327.

Ferrara, et al., "New Scoring Functions for Virtual Screening from Molecular Dynamics Simulations with a Quantum-Refined Force-Field (QRFF-MD). Application to Cyclin-Dependent Kinase 2", *J. Chem. Inf. Model.*, 2006, 46(1), 254-263.

Foye, et al., "The Preparation of Azopyrimidines and Their Metallized Derivatives", *J. Am. Pharm. Assoc.*, 1957, 46, 224-227.

Ganoub, "A Facile Approach to N-Heterocycles. The Reactions of Ylide Phosphoranes with Hydrazones", *Heterocycl. Commun.*, 2001, 7(2), 143-148.

Garg, et al., Potential Antidiabetics VIII: 4-Aryhydrazono-N'-guanylnitrate-3-methyl-2-pyrazolin-5-ones, 4-Arylazo-N'-guanylnitrate-3,5-dimethylpyrazoles, and 4-arylazo-N'-guanylnitrate-3,5-diphenylpyrazoles, *Journal of Pharmaceutical Sciences*, 1971, 60(2), 323-325.

Goldstein et al., "Specific Spot Test for Magnesium", *Mikrochim. Acta*, 1962, 50(1-2), 352-356.

Grandmougin et al, "Indigo. V. Halogenated Indigo and Derivatives", *Berichte der Deutschen Chemischen Gesellschaft*, 1914, 47, 2365-2373.

Halberkann, "Abkömmlinge der Chininsäure", *Chem. Ber.*, 1921, 54(11), 3090-3107.

Haslinger, "Action of Ethylamine on Isatine. (II)", *Berichte der Deutschen Chemischen Gesellschaft*, 1908, 41, 1444-1453.

Hassan et al., Studies on Spiro Azetidinones and Spiro Thiazolidinones, III. Synthesis of Some New Spiro Azetidinones, Spiro Thiazolidinones, Bis-Azetidinones) and bis-thiazolidinones, *Z. Naturforsch*, 1979, 34b(4), 621-623.

Heller, "New Isomerisms in the Isatin Series. IV", *Chem. Ber*, 1920, 53B, 1545-1551.

Heller, "New Reduction Stage of the Nitro Group. III", *Chem. Ber*, 1910, 43, 2892-2899.

Heller, "On the Action of Dichloracetic Acid on Aniline and its Homologues. II", *Justus Liebigs Ann. Chem.*, 1908, 358, 349-373.

Heller, "Über die Einwirkung von Dichloressigsäure auf Anilin und Homologe", *Justus Liebigs Ann. Chem.*, 1910, 375, 261-288.

Helmy, "Spectrophotometric and Polarographic Behavior of 5-Phenyl azo-2,4,6-(1H,3H,5H)pyrimidinetrione in Aqueous Ethanolic Media", *Annali di Chimica*, 1996, 86(7-8), 369-380.

Hemmerich et al., "Synthesen in der Lumiflavinreihe", *Helv. Chim. Acta*, 1956, 39, 1242-1248.

Hihara, et al., "Photo-Oxidation of Pyrazolinylazo Dyes and Analysis of Reactivity as Azo and Hydrazone Tautomers Using Semiempirical Molecular Orbital PM5 Method", *Dyes and Pigments*, 2006, 69, 151-176.

Inagaki et al. "Induction of Megakaryocytopoiesis and Thrombocytopoiesis by JTZ-132, a Novel Small Molecule with Thrombopoietin Mimetic Activities." *Blood*, 2004, 104, 58-64.

International Search Report and Written Opinion for PCT/US2005/018924 dated Nov. 4, 2006.

International Search Report and Written Opinion for PCT/US2005/038055 dated Aug. 2, 2006.

Jones, et al., "The Structures of Some 5-Pyrazolones and Derived 4-Arylazo-5-Pyrazolones", *Tetrahedron*, 1963, 19, 1497-1507.

Joshi et al., "Synthesis, $^{19}$F NMR Spectral Studies and Antibacterial Evaluation of Some New Fluorine Containing Indole Derivatives", *J. Fluorine Chem.*, 1990, 48(2), 169-188.

Kalb, et al., "Untersuchungen in der Indigo-Gruppe, V.: 5.7.5'.7'-tetrajod-indigo, 5.6.7.5'.6'.7'— Hexajod-indigo und verwandte Verbindungen", *Chem. Ber.*, 1924, 57, 2105-2117.

Kamada, et al., "Absorption Spectra of Phenolazopyrazolones in Ionization State", *Nippon Kagaku Zasshi*, 1967, 88(8), 826-830.

Kamel et al., "Monoazo Metal Complex Forming Dyes. V. Dyes Derived from Isatin", *J. Chem. U. A. R.*, 1966, 9(2), 139-144.

Katritzky et al., "2-Chloro-3H -indol-3-one and its Reactions with Nucleophiles", *J.Heterocyclic Chem.*, 1989, 26(3), 821-828.

Kaul, et al., "NMR Spectra of Azophenols and Quinone Hydrazones", *Tetrahedron Lett.*, 1966, 32, 3897-3903.

Kaupp, et al., "Waste-Free Chemistry of Diazonium Salts and Benign Separation of Coupling Products in Solid Salt Reactions", *Chem. Eur. J.*, 2002, 8(6), 1395-1406.

Kitaev et al., "Study of the Structure and Reactivity of Nitrogen Containing Derivatives of Carbonyl Compounds Communication 30. Polarographic Investigation of Products of Combination of Diazonium Salts with 1,2-Diphenyl-3,5-dioxopyrazolidine, Its 4-Lydenes, and Barbituric Acid", *Russ. Chem. Bull.*, 1968, 17(5), 940-944.

Kondrashova, et al., "Condensation of 4-(4—Hydroxycarbonylquinolin-2-yl)phenyldiazonium Chloride with $R^1 CH_2 R^2$ Compounds Containing the Activated-$CH_2$-Group", *Doklay Chemistry*, 2004, 398(1), 187-190.

Konstantinovic, et al., "UV/VIS spectrophotometric investigation of Schiff base in acid medium", *Physical Chemistry 2002, Proceedings of the International Conference on Fundamental and Applied Aspects of Physical Chemistry*, 6$^{th}$, Belgrade, Yugoslavia, Sep. 26-28, 2002, 2, 690-692.

Kroemer, et al., "Assessment of Docking Poses: Interactions-Based Accuracy Classification (IBAC) versus Crystal Structure Deviations", *J. Chem. Inf. Comput. Sci.*, 2004, 44(3), 871-881.

Kuter et al., *Proc. Natl. Acad. Sci.*, 1994, 91, 11104-11108.

Kuter et al., *The Oncologist*, 1996, 1, 98-106.

Lamb et al. "Stat protein complexes activated by interferon-γ and gp130 signaling molecules differ in their sequence preferences and transcriptional induction properties." *Nucleic Acids Research*; 23(16): 3283-3289 (1995).

Lecher, et al., "The reactions of Arylhydrazines with Diketene and the Preparation of 1-Aryl-5-methyl-3-pyrazolones", *J. Am. Chem. Soc.*, 1944, 66 1959-1963.

Li, et al., "Structure—activity Relationship Study of Oxindole-based Inhibitors of Cyclin-Dependent Kinases Based on Least-Squares Support Vector Machines", *Analytica Chimica Acta*, 2007, 581(2), 333-342.

Lok et al., Nature, 1994, 369, 565-568.

Maginnity et al., "Derivatives of o-, m- and p-Aminobenzotrifluoride", *J. Amer. Chem. Soc.*, 1951, 73(8), 3579-3580.

Marcou, et al., "Optimizing Fragment and Scaffold Docking by Use of Molecular Interaction Fingerprints", *J. Chem. Inf. Model.*, 2007, 47(1), 195-207.

Martinet, "Syntheses Dans la Serie L'Indol, Homologues du Dioxindol et de L'Isatine", *Ann. Chim. (Paris)*, 1919, (9)11, 85-111.

Martinet, et al., "Action de L'Oxime du Chloral sur les Amines Aromatiques;.Synthese D'Isatines", *Hebd. Seances Acad. Sci.*, 1921, 172, 1234-1236.

Massoud, "Synthetic Studies of Some New Derivatives Bearing Isatin Moiety", *Alex. J. Pharm. Sci.*, 2000, 14(1), 51-57.

Maysinger, et al., "Effects of Isatin N-Mannich Bases on HeLa cells", *Arzneim.-Forsch.*, 1980, 30(6), 932-935.

Metcalf, *Nature*, 1994, 369, 519-520.

Meyer, "Dibromophenylisoxazolone et Derives", *C. R. Hebd. Seances Acad. Sci.*, 1912, 1511-1514.

Meyer, "Les Matieres Colorants Azoiques de la Phenylisoxazolone", *C. R. Hebd. Seances Acad. Sci.*, 1913, 1992-1995.

Meyer, "Preparation et Proprietes de la Dibromo-4,4-phenylisoxazolone", *Ann. Chim. (Paris)*,, 1914, 314-323.

Meyer, "Sur les Matieres Colorants Azoiques de la Phenylisoxazolone", *Bull. Soc. Chim. Fr.*, 1913, 1030-1039.

Mossini, "Su Alcuni Nuovi Azoderivati Della p-Aminobenzosolfonamide", *Ann, Chimica farm.*, 1939 (Dez.) 47-53.

Mostafa, "Flame-atomic Absorption Spectrometric Determination of Chromium", *Analusis*, 1991, 19(10), 363-366.

Müller et al., "The Effects of Compounds Structurally Related to Isatin on the Monoamine Oxidase Activity of Mice Liver Homogenates", *Acta Biologica et Medica Germanica*, 1965, 14(2), 158-166.

Mustroph, "Blaue Azofarbstoffe auf der Basis von 3-Cyano-6-hydroxy-2-pyridonen", *Z. Chem.*, 1989, 29(11), 422-423.

Nesynov et al., "Arylation of monothiobarbituric acid by aryldiazonium salts", *Chem. Heterocycl. Compd.*, 1971, 7(9), 1194-1197.

Nguyen, et al., "Synthesis and biological effects of some isatin derivatives", *Tap Chi Duoc Hoc*, 1998, 12,8-10.

Nishino, et al., "Azoic Diazo Components Containing Pyrazolone Ring", *Kogyo Kagaku Zasshi*, 1959, 62(4), 552-554.

Nishino, et al., "Azoic Diazo Components Containing Pyrazolone Ring", *Bulletin of the University of Osaka Prefecture, Series A*, 1959, 7, 79-84.

Oblak, et al., "In silico Fragment-Based Discovery of lndolin-2-one Analogues as Potent DNA Gyrase Inhibitors," *Bioorg. Med. Chem. Lett.*, 2005, 15(23), 5207-10.

Olszewski, et al., "Potential Photoaffinity Labels for Tubulin. Synthesis and Evaluation of Diazocyclohexadienone and Azide Analogs of Colchicine, Combrestatin, and 3,4,5- Trimethoxybiphenyl", *J. Org. Chem.*, 1994, 59(15), 4285-4296.

Palluotto, et al., "Synthesis and Antibacterial Activity of Pyridazino[4,3-b] indole-4-carboxylic acids Carrying Different Substituents at N-2", *II Farmaco*, 2002, 57(1), 63-69.

Parkes, et al., "Reactivity of the Methylene Group in Derivatives of Phenylacetic Acid", *J. Chem. Soc.*, 1938, 1841-1845.

Piscopo et al., "Studies On Heterocyclic Compounds: Indole-2,3-dione Derivatives. VII. Variously Substituted Hydrazones with Antimicrobial Activity", *Societa Italiana Biologia Sperimentale*, 1987, 63(9), 827-832.

Popp, "Potential Anticonvulsants. IX. Some Isatin Hydrazones and Related Compounds", *J. Heterocyclic Chem.*, 1984, 21(6), 1641-1645.

Popp, "Synthesis of potential antineoplastic agents. XX. Compounds related to the 3-o-nitrophenylhydrazone of isatin", *J. Med. Chem.*, 1969, 12(1), 182-184.

Potapova et al., "Biological Activity and Mechanism of Action of 1-Glycosylisatin-3-Thiosemicarbazones", *Khimiki-Farmatsevticheskii Zhurnal*, 1984, 18(7), 785-790.

Radwan et al., "Synthesis of Diarylsulfides and Diarylsulfones Containing Pyrazoline, Isoxazoline, Pyrimidine and Condensed Phridazine Moieties", *Phosphorus, Sulfur and Silicon*, 1991, 63(3-4), 363-372.

Ram et al., "Pesticidal Mannich Bases Derived from Isatinimines", *J. Heterocyclic Chem.*, 1986, 23(5), 1367-1369.

Ram, "Application of nickel chloride to tea plants and control of blister blight", *Current Science*, 1961, 30,57-58.

Rastelli, et al., "Discovery of New Inhibitors of Aldose Reductase from Molecular Docking and Database Screening", *Bioorg. Med. Chem.*, 2002, 10(5), 1437-1450.

Research, Development and License Agreement, dated Dec. 29,1994, between SmithKline Beecham Corporation and Ligand Pharmaceuticals (with certain confidential portions omitted).

Ressy et al., "Sur Les Preparations des Homologues de L'Isatine: Preparation de la Methyl-7- bromo-5-isatine", *Bull. Soc. Chim. Fr.*, 1923, (4)33,637-640.

Revill et al., "Antithrombocytopenic Thrombopoietin Receptor Agonist", Drugs of the Future, 2006, 31(9), 767-770.

Ried et al., "Reactions with diazocarbonyl compounds. XXIX. Reaction of o-quinone diazides with active methylene compounds", *Justus Liebigs Ann. Chem*, 1968, 716,190-197.

Rupe, et al., "Das Phenylhydroxylamin-Derivat der Isatin-7-Carbonsäure ", *Helv. Chim. Acta*, 1927, 10, 926-937.

Sakamoto et al., "N-[(N-Nitrosoarylamino) Methyl] Succinimide as a New Agent Generating Aromatic Diazotate", *Chem. Pharm. Bul.*, 1977, 25(4), 731-739.

Schoutissen, "Preparation des Derives du m-Dihydrazinobenzene en Partant de la Combinaison Tetrazonium du m-Diaminobenzene", *Recl. Trav. Chim. Pays-Bas*, 1933, 52, 869-873.

Schunck; et al., "Zur Kenntniss der Rothen Isomeren des Indigotins und Über Einige Derivate des Isatins", *Chem. Ber.*, 1895, 28(1), 539-547.

Seidel et al. "Spacing of palindromic half sites as a determinant of selective STAT (signal transducers and activators of transcription) DNA binding and transcriptional activity." *Proc. Nat. Acad. Sci. USA*; 92: 3041-3045 (1995).

Sharma, "Dichloro Bis (Isatin β-Phenylhydrazone) Mercury (II)", *Current Science*, 1973, 42(3), 92.

Snavely, et al., "A study of the Structure of Hydrazones of Indole-2,3-dione and 1-Methylindole-2,3-dione with Nuclear Magnetic Resonance Spectroscopy", *J. Org. Chem.*, 1981, 46(13), 2764-2766.

Sokolowska, et al., "Synthesis and evaluation of organic pigments. 3. Studies Based on Nonmutagenic Twisted Benzidines", *Dyes and Pigments*, 2001, 48,15-27.

Somoza, et al., "Rational Design of Novel Antimicrobials: Blocking Purine Salvage in a Parasitic Protozoan" *Biochemistry*, 1998, 37(16), 5344-5348.

Sridhar, et al., "Synthesis and Antibacterial Screening of Hydrazones, Schiff and Mannich Bases of Isatin Derivatives", *Eur. J. Med. Chem.*, 2001, 36(7-8), 615-625.

Sridhar, et al., "Synthesis and Pharmacological Activities of Schiff Bases and Hydrazones of Isatin Derivatives", Indian Drugs, 2001, 38(4), 174-180.

Sridhar, et al., "Synthesis, Characterization and Pharmacological Screening of Some Isatinoid Compounds", *Indian J. Chem.*, Sec. B, 2002, 41B(3), 668-672.

Sridhar, et al., Anticonvulsant Activity of Hydrazones, Schniff and Mannich Bases of Isatin Derivatives, *European Journal of Pharmaceutical Sciences*, 2002, 16(3), 129-132.

Stahl, et al., "A Robust Clustering Method for Chemical Structures", *J. Med. Chem.*, 2005, 48(13), 4358-4366.

Stamm, "Zur Reaktion von Reaktivfarbstoffen mit Cellulose II. Natur der Bindung", *Helv. Chim. Acta*, 1963, 46,3008-3019.

Summers et al., "Structure of 3-Alkyl-4-arylazoisoxazol-5-ones and Related Compounds", *J. Chem. Soc.*, 1965, 3312-3318.

Sumpter et al., "Study of Certain Brominated Derivatives of Oxindole", *J. Am. Chem. Soc.*, 1945, 67, 1656-1658.

Tacke et al. "Sila-substitution—a useful strategy for drug design?" *New Series*; 10(4):191-197 (1986).

Taha et al., "Isatin 3-Phenylhydrazone Complexes of Some Transition Metals", *J. Chem. U. A. R.*, 1970, 13(2), 227-230.

Terent'Ev et al.,"Preparation of Bromo-, .Nitro-, and Aminoindoles and Indolines ", *J. Gen. Chem. USSR*, 1959, 29(8), 2504-2512.

Thomas, et al., "Protein Structures in Virtual Screening: A Case Study with CDK2", *J. Med. Chem.*, 2006, 49(1), 92-104.

Tirouflet et al., "Synthesis and Physicochemical Properties of Substituted Phthalonimides", *Compd. Rend.*, 1958, 246,3255-3257.

Toda, "Absorption Spectra of 1-2 Chromium(III) Complexes", *Nippon Kagaku Zasshi*, 1968, 89(1), 29-32.

Tominaga, et al., "General Model for Estimation of the Inhibition of Protein Kinases Using Monte Carlo Simulations", *J. Med. Chem.*, 2004, 47(10), 2534-2549.

Tran, et al., "5-Fluoroisatin and Its Derivatives", *Tap Chi Duoc Hoc*, 1999,11,4-5.

Urbschat, "Azo Compounds with High Activity Against Leaf Fungi", *Angew. Chem.*, 1960, 72(24), 981-985.

Vigon et al. "Molecular cloning and characterization of *MPL*, the human homolog of the v-*mpl* ncogene: Identfication of a member of the hematopoietic growth factor receptor superfamily." *Natl. Acad. Sci. USA*; 89:5640-5644 (1992).

Vine, et al., "In Vitro Cytotoxicity Evaluation of Some Substituted Isatin Derivatives", *Bioorg. Med. Chem.*, 2007, 15(2), 931-938.

Voronowa et al., "Polarographic Study of Azo derivatives of Barbituric and Thiobarbituric Acids", *J. Gen. Chem. USSR*, 1959, 29(9), 3083-3089.

Vottero, et al., "Inhibitors of Human Indoleamine 2,3-Dioxygenase Identified With a Target—Based Screen in Yeast", *Biotechnol. J.*, 2006, 1(3), 282-288.

Wending et al., *Nature*, 1994, 369,571-574.

Wendling et al., *Biotherapy*, 1998, 10(4), 269-277.

Wu, et al., "Discovery of a Novel Family of CDK Inhibitors with the Program LIDAEUS: Structural Basis for Ligand-Induced Disordering of the Activation Loop", *Structure*, 2003, 11(4), 399-410.

Wu, et al., SDOCKER: A Method Utilizing Existing X-ray Structures to Improve Docking Accuracy, *J. Med. Chem.*, 2004, 47(12), 3142-3148.

Yamamoto, et al., "$^{15}$N NMR Study of Azo-Hydrazone Tautomerism of Some Water-soluble Dyes", *Dyes and Pigments*, 1989, 11, 173-177.

Yasuda, et al., "The Structure of 2-Pyrazolin-5-one Dyes", *J. Org. Chem.*, 1966, 31(6), 1722-1725.

\* cited by examiner

THROMBOPOIETIN ACTIVITY MODULATING COMPOUNDS AND METHODS

FIELD OF THE INVENTION

The present invention relates to compounds and methods in the fields of chemistry and medicine. More specifically, the present invention relates to compounds that modulate one or more thrombopoietin activity and/or bind to thrombopoietin receptors, and to methods for making and using such compound.

BACKGROUND

Thrombopoietin (TPO), also referred to as c-Mpl ligand, mpl ligand, megapoietin, and megakaryocyte growth and development factor, is a glycoprotein that has been shown to be involved in production of platelets. See e.g., Wendling, F., et. al., Biotherapy 10(4):269-77 (1998); Kuter D. J. et al., The Oncologist, 1:98-106 (1996); Metcalf, Nature 369: 519-520 (1994), all of which are incorporated herein by reference in their entirety. TPO has been cloned and its amino acid sequence and the cDNA sequence encoding it have been described. See e.g., U.S. Pat. No. 5,766,581; Kuter, D. J. et al., Proc. Natl. Acad. Sci., 91:11104-11108 (1994); de Sauvage F. V., et al., Nature, 369: 533-538 (1994); Lok, S. et al., Nature 369:565-568 (1994); Wending, F. et al., Nature, 369: 571-574 (1994), all of which are incorporated herein by reference in their entirety.

In certain instances, TPO activity results from binding of TPO to the TPO receptor (also called MPL). The TPO receptor has been cloned and its amino acid sequence has been described. See e.g., Vigon et al., Proc. Natl. Acad. Sci., 89:5640-5644 (1992), which is incorporated herein by reference in its entirety.

In certain instances, TPO modulators may be useful in treating a variety of hematopoietic conditions, including, but not limited to, thrombocytopenia. See e.g., Baser et al. Blood 89:3118-3128 (1997); Fanucchi et al. New Engl. J. Med. 336:404-409 (1997), both of which are incorporated herein by reference in their entirety. For example, patients undergoing certain chemotherapies, including but not limited to chemotherapy and/or radiation therapy for the treatment of cancer, may have reduced platelet levels. In certain instances, treating such patients with a selective TPO modulator increases platelet levels. In certain instances, selective TPO modulators stimulate production of glial cells, which may result in repair of damaged nerve cells.

SUMMARY OF THE INVENTION

In certain embodiments, the present invention provides a compound of Formula I or II:

(I)

(II)

or a pharmaceutically acceptable salt, ester, amide, or pro drug thereof, wherein:

$R^1$ is selected from $CO_2R^{10}$, $CONR^{10}R^{11}$, $SO_3R^{10}$, and a carboxylic acid bioisostere;

$R^2$ and $R^3$ are each independently selected from hydrogen, $OR^{12}$, $NR^{12}R^{13}$, $N=R^{12}$, an optionally substituted $C_1$-$C_4$ alkyl, an optionally substituted $C_1$-$C_4$ haloalkyl, an optionally substituted $C_1$-$C_4$ heteroalkyl, an optionally substituted ring, and $(CH_2)_m R^{14}$, or $R^2$ and $R^3$ are independently absent or are taken together form an optionally substituted olefin or are linked to form an optionally substituted $C_3$-$C_8$ ring or one of $R^2$ or $R^3$ is linked to $R^1$ to form an optionally substituted $C_3$-$C_8$ ring;

$R^4$ is selected from hydrogen, F, Cl, Br, an optionally substituted $C_1$-$C_4$ alkyl, an optionally substituted $C_1$-$C_4$ haloalkyl, an optionally substituted $C_1$-$C_4$ heteroalkyl, and an optionally substituted ring;

$R^5$ is selected from hydrogen, $OR^{10}$, $SR^{10}$, $NHR^{11}$, F, and $CO_2H$;

$R^6$ is selected from hydrogen, $OR^{12}$ $NR^{12}R^{13}$, $N=R^{12}$, F, Cl, Br, an optionally substituted $C_1$-$C_4$ alkyl, an optionally substituted $C_1$-$C_4$ haloalkyl, an optionally substituted $C_1$-$C_4$ heteroalkyl, and an optionally substituted ring;

$R^7$ is selected from hydrogen, an optionally substituted $C_1$-$C_4$ alkyl, an optionally substituted $C_1$-$C_4$ haloalkyl, an optionally substituted $C_1$-$C_4$ heteroalkyl, $(CH_2)_m R^{14}$, and an optionally substituted ring;

$R^{10}$ is selected from hydrogen, an optionally substituted $C_1$-$C_4$ alkyl, an optionally substituted $C_1$-$C_4$ haloalkyl, and an optionally substituted $C_1$-$C_4$ heteroalkyl;

$R^{11}$ is selected from hydrogen, $SO_2R^{15}$, an optionally substituted $C_1$-$C_4$ alkyl, an optionally substituted $C_1$-$C_4$ haloalkyl, and an optionally substituted $C_1$-$C_4$ heteroalkyl;

$R^{12}$ and $R^{13}$ are each independently selected from hydrogen, an optionally substituted $C_1$-$C_4$ alkyl, an optionally substituted $C_1$-$C_4$ haloalkyl, an optionally substituted $C_1$-$C_4$ heteroalkyl, and $(CH_2)_m R^{14}$; or $R^{12}$ and $R^{13}$ are linked to form an optionally substituted $C_3$-$C_8$ ring;

$R^{14}$ is selected from an optionally substituted $C_6$-$C_{10}$ aryl and an optionally substituted $C_3$-$C_{10}$ heteroaryl;

$R^{15}$ is selected from hydrogen, an optionally substituted $C_1$-$C_3$ alkyl, an optionally substituted $C_1$-$C_3$ haloalkyl, and an optionally substituted $C_6$-$C_{10}$ aryl;

Z is selected from:

a 2-5 atom spacer selected from an optionally substituted $C_6$-$C_{10}$ aryl and an optionally substituted $C_3$-$C_{10}$ heteroaryl, and a spacer of 1-5 atoms selected from an optionally substituted $C_1$-$C_6$ alkyl, an optionally substituted $C_1$-$C_6$ heteroalkyl, an optionally substituted $C_1$-$C_6$ haloalkyl, an optionally substituted $C_2$-$C_6$ alkenyl, an optionally substituted $C_2$-$C_6$ heteroalkenyl, an optionally substituted $C_2$-$C_6$ haloalkenyl, an optionally substituted $C_2$-$C_6$ alkynyl, an optionally substituted $C_2$-$C_6$ heteroalkyl, O, S, and NH;

m is 0-2;

n is 0-1; and any bond represented by a dashed and solid line represents a bond selected from the group consisting of a single bond and a double bond;

provided that:

if $R^5$ is OH and $R^1$ is $CO_2R^{10}$, and Z is an aryl or heteroaryl, then at least one of $R^2$ and $R^3$ is not hydrogen or null;

if $R^5$ is OH and $R^1$ is selected from $CO_2R^{10}$, $CONR^{10}R^{11}$, $SO_3R^{10}$, a tetrazole, and $NHSO2R^{15}$, and Z is an aryl or heteroaryl, then n is 1;

if $R^5$ is OH and $R^1$ is

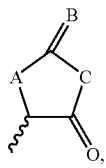

wherein A, B, and C are each independently selected from O, S, and N, and Z is an aryl or heteroaryl, then neither $R^2$ nor $R^3$ is null; and $R^7$ is a non-aromatic ring, then

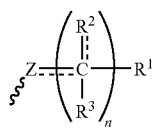

is not:

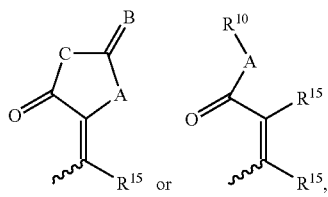

wherein A, B, and C are each independently selected from O, S, and N.

In certain embodiments, the present invention provides a compound of Formula I or II:

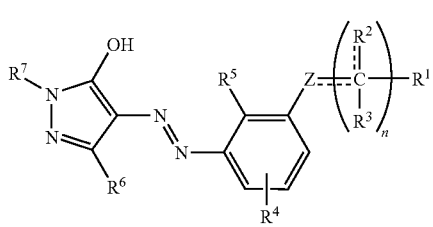

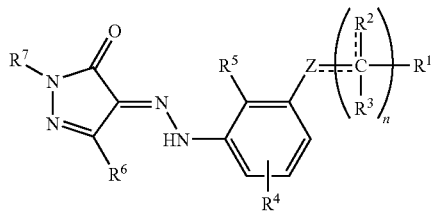

or a pharmaceutically acceptable salt, ester, amide, or prodrug thereof, wherein:

$R^1$ is selected from $CO_2R^{10}$, $CONR^{10}R^{11}$, $SO_3R^{10}$, and a carboxylic acid bioisostere;

$R^2$ and $R^3$ are each independently selected from hydrogen, $OR^{12}$, $NR^{12}R^{13}$, $N=R^{12}$, an optionally substituted $C_1$-$C_4$ alkyl, an optionally substituted $C_1$-$C_4$ haloalkyl, an optionally substituted $C_1$-$C_4$ heteroalkyl, and $(CH_2)_mR^{14}$, or $R^2$ and $R^3$ are independently absent or $R^2$ and $R^3$ taken together form an optionally substituted olefin or are linked to form an optionally substituted $C_3$-$C_8$ ring or one of $R^2$ or $R^3$ is linked to $R^1$ to form an optionally substituted $C_3$-$C_8$ ring;

$R^4$ is selected from hydrogen, F, Cl, Br, an optionally substituted $C_1$-$C_4$ alkyl, an optionally substituted $C_1$-$C_4$ haloalkyl, and an optionally substituted $C_1$-$C_4$ heteroalkyl;

$R^5$ is selected from hydrogen, $OR^{10}$, $SR^{10}$, $NHR^{11}$, and $CO_2H$;

$R^6$ is selected from hydrogen, $OR^{12}$, $NR^{12}R^{13}$, $N=R^{12}$, F, Cl, Br, an optionally substituted $C_1$-$C_4$ alkyl, an optionally substituted $C_1$-$C_4$ haloalkyl, and an optionally substituted $C_1$-$C_4$ heteroalkyl;

$R^7$ is selected from hydrogen, an optionally substituted $C_1$-$C_4$ alkyl, an optionally substituted $C_1$-$C_4$ haloalkyl, an optionally substituted $C_1$-$C_4$ heteroalkyl, and $(CH_2)_mR^{14}$;

$R^{10}$ is selected from hydrogen, an optionally substituted $C_1$-$C_4$ alkyl, an optionally substituted $C_1$-$C_4$ haloalkyl, and an optionally substituted $C_1$-$C_4$ heteroalkyl;

$R^{11}$ is selected from hydrogen, $SO_2R^{15}$, an optionally substituted $C_1$-$C_4$ alkyl, an optionally substituted $C_1$-$C_4$ haloalkyl, and an optionally substituted $C_1$-$C_4$ heteroalkyl;

$R^{12}$ and $R^{13}$ are each independently selected from hydrogen, an optionally substituted $C_1$-$C_4$ alkyl, an optionally substituted $C_1$-$C_4$ haloalkyl, an optionally substituted $C_1$-$C_4$ heteroalkyl, and $(CH_2)_mR^{14}$; or $R^{12}$ and $R^{13}$ are linked to form an optionally substituted $C_3$-$C_8$ ring;

$R^{14}$ is selected from an optionally substituted $C_6$-$C_{10}$ aryl and an optionally substituted $C_3$-$C_{10}$ heteroaryl;

$R^{15}$ is selected from hydrogen, an optionally substituted $C_1$-$C_3$ alkyl, an optionally substituted $C_1$-$C_3$ haloalkyl, and an optionally substituted $C_6$-$C_{10}$ aryl;

Z is selected from:

a 2-5 atom spacer selected from an optionally substituted $C_6$-$C_{10}$ aryl and an optionally substituted $C_3$-$C_{10}$ heteroaryl, and a 1-5 atom spacer selected from an optionally substituted $C_1$-$C_6$ alkyl, an optionally substituted $C_1$-$C_6$ heteroalkyl, an optionally substituted $C_1$-$C_6$ haloalkyl, an optionally substituted $C_2$-$C_6$ alkenyl, an optionally substituted $C_2$-$C_6$ heteroalkenyl, an optionally substituted $C_2$-$C_6$ haloalkenyl, an optionally substituted $C_2$-$C_6$ alkynyl, and an optionally substituted $C_2$-$C_6$ heteroalkyl;

m is 0-2;

n is 0 or 1; and any bond represented by a dashed and solid line represents a bond selected from the group consisting of a single bond and a double bond;

provided that:

if $R^5$ is OH and $R^1$ is selected from $CO_2R^{10}$, $CONR^{10}R^{11}$, $SO_3R^{10}$, tetrazole, and $NHSO_2R^{15}$, then at least one of $R^2$ and $R^3$ is not hydrogen, n is 1, and Z is selected from an optionally substituted $C_6$-$C_{10}$ aryl, an optionally substituted $C_3$-$C_8$ heteroaryl, an optionally substituted $C_1$-$C_6$ non-straight-chain-alkoxy-heteroalkyl, and an optionally substituted $C_2$-$C_6$ heteroalkenyl.

In certain embodiments, the present invention provides a compound of Formula I or II, above, wherein $R^1$ is a carboxylic acid bioisostere selected from tetrazole, $NHSO_2R^{15}$, $OC(S)NR^{10}R^{11}$, $SC(O)NR^{10}R^{11}$, thiazolidinedione, oxazolidinedione, and 1-oxa-2,4-diazolidine-3,5-dione.

In certain embodiments, the present invention provides a compound of Formula I or II, above, wherein if $R^5$ is OH and $R^1$ selected from $CO_2R^{10}$, $CONR^{10}R^{11}$, $SO_3R^{10}$, a tetrazole, and $NHSO_2R^{15}$, then Z is selected from:

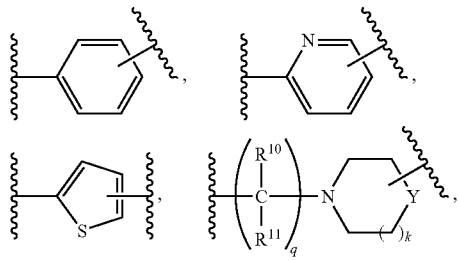

—$(CR^2R^3)_jO$—, and
—$(CR^{10}R^{11})_qNR^{15}$—;

wherein;
Y is selected from O, S, $NR^{10}$, and $CH_2$;
j is 1-3;
q is 0-2; and
k is 0 or 1.

In certain embodiments, the invention provides a compound selected from: (±)-2-(3'-{N'-[1-(3,4-Dimethylphenyl)-3-methyl-5-oxo-1,5-dihydro-pyrazol-4-ylidene]-hydrazino}-2'-hydroxy-biphenyl-3-yl)-propionic acid (Compound 101); 2-(5'-Chloro-3'-{N'-[1-(3,4-dimethyl-phenyl)-3-methyl-5-oxo-1,5-dihydro-pyrazol-4-ylidene]-hydrazino}-2'-hydroxy-biphenyl-3-yl)-2-methyl-propionic acid (Compound 102); (±)-2-(3'-{N'-[1-(3,4-Dimethylphenyl)-3-methyl-5-oxo-1,5-dihydro-pyrazol-4-ylidene]-hydrazino}-2'-hydroxy-biphenyl-3-yl)-3-phenylpropionic acid (Compound 103); (±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-3-yl)-butyric acid (Compound 104); (±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionic acid (Compound 105); (±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-thiopropionic acid (Compound 106); (±)-2-(3'-{N'-[1-(3,4-Dimethyl-phenyl)-3-methyl-5-oxo-1,5-dihydro-pyrazol-4-ylidene]-hydrazino}-5'-fluoro-2'-hydroxy-biphenyl-4-yl)-propionic acid (Compound 107); 3-{N'-[1-(3,4-Dimethyl-phenyl)-3-methyl-5-oxo-1,5-dihydro-pyrazol-4-ylidene]-hydrazino}-biphenyl-2,3'-dicarboxylic acid (Compound 108); (±)-2-(3'-{N'-[1-(3,4-Dimethyl-phenyl)-3-methyl-5-oxo-1,5-dihydro-pyrazol-4-ylidene]-hydrazino}-2'-hydroxy-5'-methyl-biphenyl-4-yl)-propionic acid (Compound 109); 2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-2-methyl-propionic acid (Compound 110); (±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-hexanoic acid (Compound 111); (±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-3-methyl-butyric acid (Compound 112); (±)-2-(S)-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionic acid (Compound 113); (±)-2-(R)-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionic acid (Compound 114); (3'-{N'-[1-(3,4-Dimethyl-phenyl)-3-methyl-5-oxo-1,5-dihydro-pyrazol-4-ylidene]-hydrazino}-2'-hydroxy-biphenyl-4-yloxy)-acetic acid (Compound 115); (±)-2-(3'-{N'-[1-(3,4-Dimethyl-phenyl)-3-methyl-5-oxo-1,5-dihydro-pyrazol-4-ylidene]-hydrazino}-5'-fluoro-2'-hydroxy-biphenyl-3-yl)-propionic acid (Compound 116); (±)-{[2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionyl]-methyl-amino}acetic acid (Compound 117); (±)-{[2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionyl]-methyl-amino}-acetic acid ethyl ester (Compound 118); (±)-4-({5-Chloro-2-hydroxy-4'-[1-(1H-tetrazol-5-yl)-ethyl]-biphenyl-3-yl}-hydrazono)-2-(3,4-dimethyl-phenyl)-5-methyl-2,4-dihydro-pyrazol-3-one (Compound 119); (±)-2-(3,4-Dimethyl-phenyl)-4-({2-hydroxy-4'-[1-(1H-tetrazol-5-yl)-ethyl]-biphenyl-3-yl}-hydrazono)-5-methyl-2,4-dihydro-pyrazol-3-one (Compound 120); (±)-2-(2'-Hydroxy-3'-{N-[3-methyl-5-oxo-1-(4-propyl-phenyl)-1,5-dihydro-pyrazol-4-ylidene]-hydrazino}-biphenyl-4-yl)-propionic acid (Compound 121); 3'-{N'-[1(3,4-Dimethyl-phenyl)-3-methyl-5-oxo-1,5-dihydro-pyrazol-4-ylidene]-hydrazino}-2'-fluoro-biphenyl-3-carboxylic acid (Compound 122); 2-(3'-{N'-[1-(3,4-Dimethyl-phenyl)-3-methyl-5-oxo-1,5-dihydro-pyrazol-4-ylidene]-hydrazino}-2'-hydroxy-5'-methyl-biphenyl-3-yloxy)-2-methyl-propionic acid (Compound 123); [(3'-{N'-[1-(3,4-Dimethyl-phenyl)-3-methyl-5-oxo-1,5-dihydro-pyrazol-4-ylidene]-hydrazino}-2'-hydroxy-biphenyl-3-carbonyl)-amino]-acetic acid (Compound 124); [(3'-{N'-[1-(3,4-Dimethyl-phenyl)-3-methyl-5-oxo-1,5-dihydro-pyrazol-4-ylidene]-hydrazino}-2'-hydroxy-biphenyl-3-carbonyl)-amino]-acetic acid ethyl ester (Compound 125); (±)-(3'-{N'-[-(3,4-Dimethyl-phenyl)-3-methyl-5-oxo-1,5-dihydro-pyrazol-4-ylidene]-hydrazino}-2'-hydroxy-biphenyl-4-yl)-methoxy-acetic acid (Compound 126); (±)-2-(5'-Chloro-3'-{N'-[1-(3,4-dimethyl-phenyl)-3-methyl-5-oxo-1,5-dihydro-pyrazol-4-ylidene]-hydrazino}-2'-hydroxy-biphenyl-3-yloxy)-butyric acid (Compound 127); 3'-{N'-[1-(3,4-Dimethyl-phenyl)-3-methyl-5-oxo-1,5-dihydro-pyrazol-4-ylidene]-hydrazino}-2'-methoxy-biphenyl-3-carboxylic acid (Compound 128); (±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-butyric acid (Compound 129); (±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yloxy)-propionic acid (Compound 130); 2-(5'-Chloro-3'-{N'-[1-(3,5-dimethyl-phenyl)-3-methyl-5-oxo-1,5-dihydro-pyrazol-4-ylidene]-hydrazino}-2'-hydroxy-biphenyl-3-yl)-2-methyl-propionic acid (Compound 131); and a pharmaceutically acceptable salt, ester, or prodrug of any of those compounds.

In certain embodiments, a compound of Formula I or II is a selective TPO modulator. In certain such embodiments, a compound of Formula I or II is a TPO mimic.

In certain embodiments, the invention provides methods for modulating a TPO activity. Certain such methods comprise contacting a cell with one or more compounds of the present invention. Such methods include, but are not limited to, contacting TPO and/or a TPO receptor with one or more compounds of the present invention.

In certain embodiments, the invention provides a method for identifying a compound that is capable of modulating TPO activity comprising: contacting a cell capable of a TPO activity with a compound of the present invention; and b) monitoring an effect on the cell. In certain such embodiments, the cell expresses a TPO receptor.

In certain embodiments, the invention provides methods of treating a patient comprising administering to the patient a compound of the present invention. In certain embodiments, such a patient suffers from thrombocytopenia. In certain embodiments, one or more compounds of the present invention are administered to a patient before, during or after chemotherapy, bone marrow transplantation, and/or radiation therapy. In certain embodiments, one or more compounds of the invention are administered to a patient suffering from aplastic anemia, bone marrow failure, and/or idiopathic thrombocytopenia. In certain embodiments, one or more compounds of the present invention are administered to a patient suffering from a disease of the nervous system. In certain embodiments, one or more compounds of the present invention are administered to a patient suffering from amyotrophic lateral sclerosis, multiple sclerosis, or multiple dystrophy. In certain embodiments, one or more compounds of the present invention are administered to a patient with a nerve injury, including, but not limited to, a spinal cord injury.

In certain embodiments, the invention provides pharmaceutical compositions comprising: i) a physiologically acceptable carrier, diluent, or excipient, or a combination thereof, and ii) one or more compounds of the present invention.

In certain embodiments, the invention provides a selective TPO modulator. In certain embodiments, the invention provides a selective TPO receptor agonist. In certain embodiments, the invention provides a selective TPO receptor antagonist. In certain embodiments, the invention provides a selective TPO partial agonist. In certain embodiments, the invention provides a selective TPO receptor binding compound. In certain embodiments, the invention provides a TPO mimic.

DETAILED DESCRIPTION

It is to be understood that both the foregoing general description and the following detailed description are exemplary and explanatory only and are not restrictive of the invention claimed. In this application, the use of the singular includes the plural unless specifically stated otherwise. In this application, the use of "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definitions

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients. Standard techniques may be used for recombinant DNA, oligonucleotide synthesis, and tissue culture and transformation (e.g., electroporation, lipofection). Reactions and purification techniques may be performed e.g., using kits according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference in its entirety for any purpose.

As used herein, the following terms are defined with the following meanings, unless expressly stated otherwise.

The term "selective binding compound" refers to a compound that selectively binds to any portion of one or more target.

The term "selective TPO receptor binding compound" refers to a compound that selectively binds to any portion of a TPO receptor.

The term "selectively binds" refers to the ability of a selective binding compound to bind to a target receptor with greater affinity than it binds to a non-target receptor. In certain embodiments, selective binding refers to binding to a target with an affinity that is at least 10, 50, 100, 250, 500, or 1000 times greater than the affinity for a non-target.

The term "target receptor" refers to a receptor or a portion of a receptor capable of being bound by a selective binding compound. In certain embodiments, a target receptor is a TPO receptor.

The term "modulator" refers to a compound that alters an activity. For example, a modulator may cause an increase or decrease in the magnitude of a certain activity compared to the magnitude of the activity in the absence of the modulator. In certain embodiments, a modulator is an inhibitor, which decreases the magnitude of one or more activities. In certain embodiments, an inhibitor completely prevents one or more biological activities. In certain embodiments, a modulator is an activator, which increases the magnitude of at least one activity. In certain embodiments the presence of a modulator results in a activity that does not occur in the absence of the modulator.

The term "selective modulator" refers to a compound that selectively modulates a target activity.

The term "selective TPO modulator" refers to a compound that selectively modulates at least one TPO activity. The term selective TPO modulator includes, but is not limited to "TPO mimic" which refers to a compound, the presence of which results in at least one TPO activity. TPO mimics are described in WO 03/103686A1 and WO 01/21180, both of which are incorporated herein by reference in their entirety.

The term "selectively modulates" refers to the ability of a selective modulator to modulate a target activity to a greater extent than it modulates a non-target activity.

The term "target activity" refers to a biological activity capable of being modulated by a selective modulator. Certain exemplary target activities include, but are not limited to, binding affinity, signal transduction, enzymatic activity, the proliferation and/or differentiation of progenitor cells, generation of platelets, and alleviation of symptoms of a disease or condition.

The term "TPO activity" refers to a biological activity that results, either directly or indirectly from the presence of TPO. Exemplary TPO activities include, but are not limited to, proliferation and or differentiation of progenitor cells to produce platelets; hematopoiesis; growth and/or development of glial cells; repair of nerve cells; and alleviation of thrombocytopenia.

The term "thrombocytopenia" refers to a condition wherein the concentration of platelets in the blood of a patient is below what is considered normal for a healthy patient. In certain embodiments, thrombocytopenia is a platelet count less than 450,000, 400,000, 350,000, 300,000, 250,000, 200,000, 150,000, 140,000, 130,000, 120,000, 110,000, 100,000, 75,000, or 50,000 platelets per microliter of blood.

The term "receptor mediated activity" refers to any biological activity that results, either directly or indirectly, from binding of a ligand to a receptor.

The term "agonist" refers to a compound, the presence of which results in a biological activity of a receptor that is the same as the biological activity resulting from the presence of a naturally occurring ligand for the receptor.

The term "partial agonist" refers to a compound the presence of which results in a biological activity of a receptor that is of the same type as that resulting from the presence of a naturally occurring ligand for the receptor, but of a lower magnitude.

The term "antagonist" refers to a compound, the presence of which results in a decrease in the magnitude of a biological activity of a receptor. In certain embodiments, the presence of an antagonist results in complete inhibition of a biological activity of a receptor.

The term "alkyl" refers to an aliphatic hydrocarbon group. An alkyl may be a "saturated alkyl," which means that it does not contain any alkene or alkyne groups. An alkyl group may be an "unsaturated alkyl," which means that it comprises at least one alkene or alkyne group. An alkyl, whether saturated or unsaturated, may be branched or straight chain. Alkyls may be substituted or unsubstituted. Alkyls include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like, each of which may be optionally substituted.

In certain embodiments, an alkyl comprises 1 to 20 carbon atoms (whenever it appears herein, a numerical range such as "1 to 20" refers to each integer in the given range; e.g., "1 to 20 carbon atoms" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated).

The term "lower alkyl" refers to an alkyl comprising 1 to 5 carbon atoms. The term "medium alkyl" refers to an alkyl comprising 5 to 10 carbon atoms. An alkyl may be designated as "$C_1$-$C_4$ alkyl" or similar designations. By way of example only, "$C_1$-$C_4$ alkyl" indicates an alkyl having one, two, three, or four carbon atoms, e.g., the alkyl is selected from methyl, ethyl, propyl, iso-propyl, n-butyl, iso-butyl, sec-butyl, t-butyl, ethenyl, propenyl, butenyl, ethynyl, propynyl, and butynyl.

The term "alkenyl" refers to an alkyl group comprising at least one carbon-carbon double bond.

The term "alkynyl" refers to an alkyl group comprising at least one carbon-carbon triple bond.

The term "haloalkyl" refers to an alkyl in which at least one hydrogen atom is replaced with a halogen atom. In certain of the embodiments in which two or more hydrogen atom are replaced with halogen atoms, the halogen atoms are all the same as one another. In certain of such embodiments, the halogen atoms are not all the same as one another.

The term "heteroalkyl" refers to a group comprising an alkyl and one or more heteroatoms. Certain heteroalkyls are acylalkyls, in which the one or more heteroatoms are within an alkyl chain. Examples of heteroalkyls include, but are not limited to, $CH_3C(=O)CH_2—$, $CH_3C(=O)CH_2CH_2—$, $CH_3CH_2C(=O)CH_2CH_2—$, $CH_3C(=O)CH_2CH_2CH_2—$, $CH_3OCH_2CH_2—$, $CH_3NHCH_2—$, and the like.

The term "straight-chain alkoxy" refers to a group comprising the formula: $—(CH_2)_pO—$ wherein p is any integer. Straight-chain alkoxy does not include substituted or branched alkoxy groups.

The term "non-straight-chain-alkoxy-heteroalkyl" refers to any heteroalkyl that is not a straight-chain alkoxy heteroalkyl. Thus, for example, non-straight-chain-alkoxy heteroalkyls include, but are not limited to: 2,2-isopropyloxy; 1,2-propyloxy; 1,1-ethyloxy; methylamino; ethylaamino; propylamino; methylpyrrolidino; and methylpiperidino.

The term "olefin" refers to a $C=C$ bond.

The term "heterohaloalkyl" refers to a heteroalkyl in which at least one hydrogen atom is replaced with a halogen atom.

The term "carbocycle" refers to a group comprising a covalently closed ring, wherein each of the atoms forming the ring is a carbon atom. Carbocylic rings may be formed by three, four, five, six, seven, eight, nine, or more than nine carbon atoms. Carbocycles may be optionally substituted.

The term "heterocycle" refers to a group comprising a covalently closed ring wherein at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). In heterocyclic rings comprising two or more heteroatoms, those two or more heteroatoms may be the same or different from one another. Heterocycles may be optionally substituted. Binding to a heterocycle can be at a heteroatom or via a carbon atom. For example, binding for benzo-fused derivatives, may be via a carbon of the benzenoid ring. Examples of heterocycles include, but are not limited to the following:

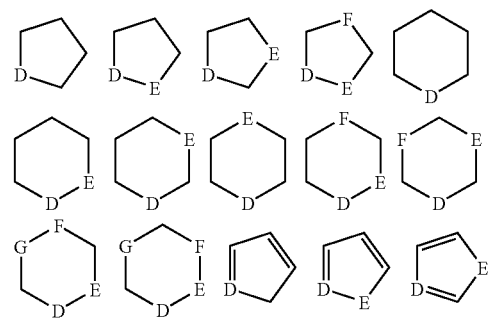

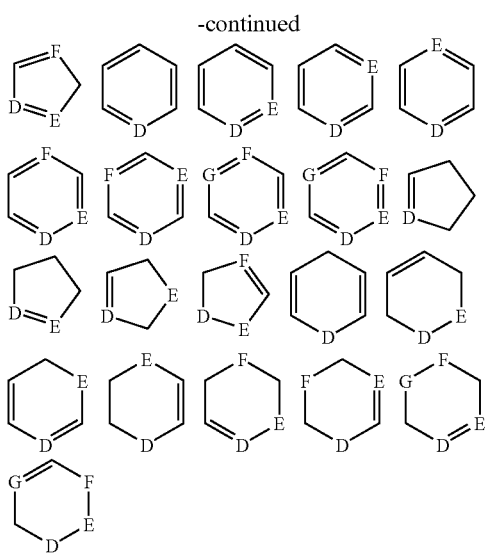

wherein D, E, F, and G independently represent a heteroatom. Each of D, E, F, and G may be the same or different from one another.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "aromatic" refers to a group comprising a covalently closed ring having a delocalized π-electron system. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_{1-6}$ alkoxy, a $C_{1-6}$ alkyl, a $C_{1-6}$ hydroxyalkyl, a $C_{1-6}$ aminoalkyl, a $C_{1-6}$ alkylamino, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "aryl" refers to an aromatic group wherein each of the atoms forming the ring is a carbon atom. Aryl rings may be formed by five, six, seven, eight, nine, or more than nine carbon atoms. Aryl groups may be optionally substituted.

The term "heteroaryl" refers to an aromatic group wherein at least one atom forming the aromatic ring is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O-$C_{1-6}$-alkyl, $C_{1-6}$-alkyl, hydroxy-$C_{1-6}$-alkyl, and amino-$C_{1-6}$-alkyl.

The term "non-aromatic ring" refers to a group comprising a covalently closed ring that does not have a delocalized π-electron system.

The term "cycloalkyl" refers to a group comprising a non-aromatic ring wherein each of the atoms forming the ring is a carbon atom. Cycloalkyl rings may be formed by three, four, five, six, seven, eight, nine, or more than nine carbon atoms. Cycloalkyls may be optionally substituted. In certain embodiments, a cycloalkyl comprises one or more unsaturated bonds. Examples of cycloalkyls include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene.

The term "non-aromatic heterocycle" refers to a group comprising a non-aromatic ring wherein one or more atoms forming the ring is a heteroatom. Non-aromatic heterocyclic rings may be formed by three, four, five, six, seven, eight, nine, or more than nine atoms. Non-aromatic heterocycles may be optionally substituted. In certain embodiments, non-aromatic heterocycles comprise one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidinone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "arylalkyl" refers to a group comprising an aryl group bound to an alkyl group.

The term "carbocycloalkyl" refers to a group comprising a carbocyclic cycloalkyl ring. Carbocycloalkyl rings may be formed by three, four, five, six, seven, eight, nine, or more than nine carbon atoms. Carbocycloalkyl groups may be optionally substituted.

The term "ring" refers to any covalently closed structure. Rings include, for example, carbocycles (e.g., aryls and cycloalkyls), heterocycles (e.g., heteroaryls and non-aromatic heterocycles), aromatics (e.g., aryls and heteroaryls), and non-aromatics (e.g., cycloalkyls and non-aromatic heterocycles). Rings may be optionally substituted. Rings may form part of a ring system.

The term "ring system" refers to two or more rings, wherein two or more of the rings are fused. The term "fused" refers to structures in which two or more rings share one or more bonds.

The term "carboxylic acid bioisostere" refers to a group that is biologically equivalent to a carboxylic acid. For example, carboxylic acid bioisosteres include, but are not limited to, tetrazole, $NHSO_2R^{15}$, $OC(S)NR^{10}R^{11}$, $SC(O)NR^{10}R^{11}$, thiazolidinedione, oxazolidinedione, and 1-oxa-2,4-diazolidine-3,5-dione. In certain embodiments, a carboxylic acid bioisoster comprises the following structure:

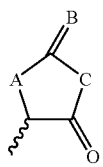

wherein A, B, and C are each independently selected from O, S, and N.

The term "spacer" refers to an atom or group of atoms that separate two or more groups from one another by a desired number of atoms. For example, in certain embodiments, it may be desirable to separate two or more groups by one, two, three, four, five, six, or more than six atoms. In such embodiments, any atom or group of atoms may be used to separate those groups by the desired number of atoms. Spacers are optionally substituted. In certain embodiments, a spacer comprises saturated or unsaturated alkyls, heteroalkyls and/or haloalkyls. In certain embodiments, a spacer comprises atoms that are part of a ring.

Solely for the purposes of illustration, and without limiting the above definition, some examples of spacers are provided. Examples of 1 atom spacers include, but are not limited to, the following:

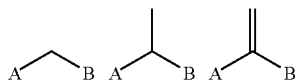

where A and B represent groups which are separated by the desired number of atoms. Examples of 2 atom spacers include, but are not limited to, the following:

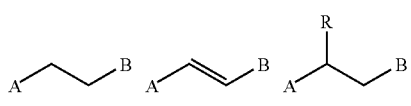

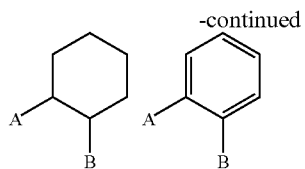

where A and B represent groups which are separated by the desired number of atoms.

Examples of 3 atom spacers include, but are not limited to, the following:

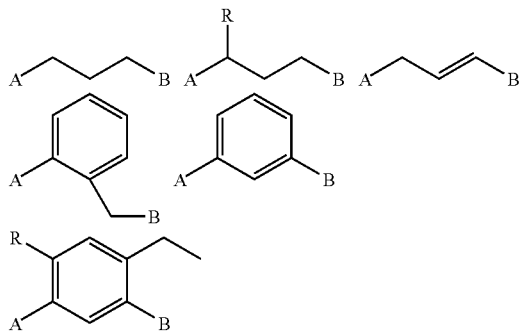

where A and B represent groups which are separated by the desired number of atoms. As is evident from the above examples, the atoms that create the desired separation may themselves be part of a group. That group may be, for example, an alkyl, heteroalkyl, haloalkyl, heterohaloalkyl, cycloalkyl, aryl, arylalkyl, heteroaryl, non-aromatic heterocycle, or substituted alkyl all of which are optionally substituted. Thus the term "1-5 atom spacer" refers to a spacer that separates two groups by 1, 2, 3, 4, or 5 atoms and does not indicate the total size of the group that constitutes the spacer.

The substituent "R" appearing by itself and without a number designation refers to a substituent selected from alkyl, cycloalkyl, aryl, heteroaryl (bonded through a ring carbon) and non-aromatic heterocycle (bonded through a ring carbon).

The term "O-carboxy" refers to a group of formula RC(=O)O—.

The term "C-carboxy" refers to a group of formula —C(=O)OR.

The term "acetyl" refers to a group of formula —C(=O)CH₃.

The term "trihalomethanesulfonyl" refers to a group of formula $X_3CS(=O)_2$— where X is a halogen.

The term "cyano" refers to a group of formula —CN.

The term "isocyanato" refers to a group of formula —NCO.

The term "thiocyanato" refers to a group of formula —CNS.

The term "isothiocyanato" refers to a group of formula —NCS.

The term "sulfonyl" refers to a group of formula —S(=O)—R.

The term "S-sulfonamido" refers to a group of formula —S(=O)₂NR.

The term "N-sulfonamido" refers to a group of formula RS(=O)₂NH—.

The term "trihalomethanesulfonamido" refers to a group of formula $X_3CS(=O)_2NR$—.

The term "O-carbamyl" refers to a group of formula —OC(=O)—NR.

The term "N-carbamyl" refers to a group of formula ROC(=O)NH—.

The term "O-thiocarbamyl" refers to a group of formula —OC(=S)—NR.

The term "N-thiocarbamyl" refers to a group of formula ROC(=S)NH—.

The term "C-amido" refers to a group of formula —C(=O)—NR$_2$.

The term "N-amido" refers to a group of formula RC(=O)NH—.

The term "ester" refers to a chemical moiety with formula —(R)$_n$—COOR', where R and R' are independently selected from alkyl, cycloalkyl, aryl, heteroaryl (bonded through a ring carbon) and non-aromatic heterocycle (bonded through a ring carbon), where n is 0 or 1.

The term "amide" refers to a chemical moiety with formula —(R)$_n$—C(O)NHR' or —(R)$_n$—NHC(O)R', where R and R' are independently selected from alkyl, cycloalkyl, aryl, heteroaryl (bonded through a ring carbon) and heteroalicyclic (bonded through a ring carbon), where n is 0 or 1. In certain embodiments, an amide may be an amino acid or a peptide.

The terms "amine," "hydroxy," and "carboxyl" include such groups that have been esterified or amidified. Procedures and specific groups used to achieve esterification and amidification are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

Unless otherwise indicated, the term "optionally substituted," refers to a group in which none, one, or more than one of the hydrogen atoms has been replaced with one or more group(s) individually and independently selected from: alkyl, heteroalkyl, haloalkyl, heteroholoalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives of amino groups. Such protective derivatives (and protecting groups that may form such protective derivatives) are known to those of skill in the art and may be found in references such as Greene and Wuts, above. In embodiments in which two or more hydrogen atoms have been substituted, the substituent groups may together form a ring.

The term "carrier" refers to a compound that facilitates the incorporation of another compound into cells or tissues. For example, dimethyl sulfoxide (DMSO) is a commonly used carrier for improving incorporation of certain organic compounds into cells or tissues.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "therapeutically effective amount" refers to an amount of a pharmaceutical agent sufficient to achieve a desired therapeutic effect.

The term "prodrug" refers to an pharmaceutical agent that is converted from a less active form into a corresponding more active form in vivo.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g., compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

The term "tissue-selective" refers to the ability of a compound to modulate a biological activity in one tissue to a greater or lesser degree than it modulates a biological activity in another tissue. The biological activities in the different tissues may be the same or they may be different. The biological activities in the different tissues may be mediated by the same type of target receptor. For example, in certain embodiments, a tissue-selective compound may modulate receptor mediated biological activity in one tissue and fail to modulate, or modulate to a lesser degree, receptor mediated biological activity in another tissue type.

The term "monitoring" refers to observing an effect or absence of any effect. In certain embodiments, one monitors cells after contacting those cells with a compound of the present invention. Examples of effects that may be monitored include, but are not limited to, changes in cell phenotype, cell proliferation, receptor activity, or the interaction between a receptor and a compound known to bind to the receptor.

The term "cell phenotype" refers to physical or biological characteristics. Examples of characteristics that constitute phenotype include, but are not limited to, cell size, cell proliferation, cell differentiation, cell survival, apoptosis (cell death), or the utilization of a metabolic nutrient (e.g., glucose uptake). Certain changes or the absence of changes in cell phenotype are readily monitored using techniques known in the art.

The term "cell proliferation" refers to the rate at which cells divide. In certain embodiments, cells are in situ in an organism. In certain embodiments, cells are grown in vitro in a vessel. The number of cells growing in a vessel can be quantified by a person skilled in the art (e.g, by counting cells in a defined area using a microscope or by using laboratory apparatus that measure the density of cells in an appropriate medium). One skilled in that art can calculate cell proliferation by determining the number of cells at two or more times.

The term "contacting" refers to bringing two or more materials into close enough proximity that they may interact. In certain embodiments, contacting can be accomplished in a vessel such as a test tube, a petri dish, or the like. In certain embodiments, contacting may be performed in the presence of additional materials. In certain embodiments, contacting may be performed in the presence of cells. In certain of such embodiments, one or more of the materials that are being contacted may be inside a cell. Cells may be alive or may dead. Cells may or may not be intact.

Certain Compounds

Certain compounds that modulate one or more TPO activity and/or bind to TPO receptors play a role in health. In certain embodiments, compounds of the present invention are useful for treating any of a variety of diseases or conditions.

In certain embodiments, the present invention provides selective TPO modulators. In certain embodiments, the invention provides selective TPO receptor binding agents. In certain embodiments, the invention provides methods of making and methods of using selective TPO modulators and/or selective TPO receptor binding agents. In certain embodiments, selective TPO modulators are agonists, partial agonists, and/or antagonists for the TPO receptor.

In certain embodiments, the present invention relates to compounds of Formula I or II:

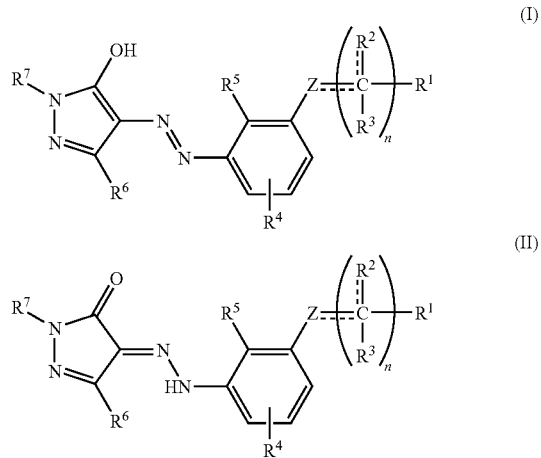

or a pharmaceutically acceptable salt, ester, amide, or prodrug thereof

In certain embodiments, $R^1$ is selected from $CO_2R^{10}$, $CONR^{10}R^{11}$, $SO_3R^{10}$, and a carboxylic acid bioisostere. In certain such embodiments, $R^1$ is selected from a carboxylic acid bioisostere selected from tetrazole, $NHSO_2R^{15}$, $OC(S)NR^{10}R^{11}$, $SC(O)NR^{10}R^{11}$, thiazolidinedione, oxazolidinedione, and 1-oxa-2,4-diazolidine-3,5-dione. In certain embodiments, a carboxylic acid bioisoster comprises the following structure:

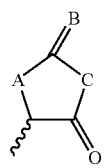

wherein A, B, and C are each independently selected from O, S, and N.

In certain embodiments, $R^2$ and $R^3$ are each independently selected from hydrogen, a halogen, $OR^{12}$, $NR^{12}R^{13}$, $N=R^{12}$, a ring, $(CH_2)_mR^{14}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_3$-$C_8$ heterocycle, an optionally substituted an optionally substituted $C_6$-$C_{10}$ aryl, and an optionally substituted an optionally substituted $C_3$-$C_{10}$ heteroaryl. In certain embodiments, $R^2$ and/or $R^3$ is an optionally substituted $C_1$-$C_8$ alkyl or an optionally substituted $C_3$-$C_8$ cycloalkyl that is fully saturated. In certain embodiments, $R^2$ and/or $R^3$ is an optionally substituted $C_1$-$C_8$ alkyl or an optionally substituted $C_3$-$C_8$ cycloalkyl that is not fully saturated. In certain such embodiments, $R^2$ and/or $R^3$ is selected from an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^2$ and/or $R^3$ is selected from an optionally substituted methyl, ethyl propyl isopropyl, butyl, sec-butyl, and tert-butyl. In certain embodiments, $R^2$ and/or $R^3$ is methyl. In certain embodiments, $R^2$ and/or $R^3$ is trifluoromethyl. In certain of the embodiments where $R^2$ and/or $R^3$ is a halogen, $R^2$ and/or $R^3$ is F or Cl. In certain embodiments, $R^2$ is methyl. In certain embodiments $R^3$ is methyl. In certain embodiments, $R^2$ is methyl and $R^3$ is methyl. In certain embodiments, at least one of $R^2$ and $R^3$ is not methyl. In certain embodiments, at least one of $R^2$ and $R^3$ is not hydrogen. In certain embodiments, if $R^2$ is hydrogen, then $R^3$ is not methyl. In certain embodiments, $R^2$ or $R^3$ are absent.

In certain embodiments, $R^2$ and $R^3$ together form an optionally substituted olefin. In certain embodiments, $R^2$ and $R^3$ are linked together, resulting in a ring formed by $R^2$, $R^3$, the carbon atom to which both $R^2$ and $R^3$ are bound, and the linker. In certain embodiments, the linker is selected from an optionally substituted $C_1$-$C_6$ alkyl, an optionally substituted $C_1$-$C_6$ heteroalkyl, an optionally substituted $C_1$-$C_6$ haloalkyl, and an optionally substituted $C_1$-$C_6$ heterohaloalkyl. In certain embodiments, $R^2$ or $R^3$ are linked to $R^1$, resulting in a ring formed by $R^2$ or $R^3$, $R^1$, the carbon atom to which both $R^2$ or $R^3$ and $R^1$ are bound, and the linker.

In certain embodiments, $R^4$ is selected from hydrogen, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_3$-$C_8$ heterocycle, an optionally substituted an optionally substituted $C_6$-$C_{10}$ aryl, and an optionally substituted an optionally substituted $C_3$-$C_{10}$ heteroaryl. In certain embodiments, $R^4$ is an optionally substituted $C_1$-$C_8$ alkyl or an optionally substituted $C_3$-$C_8$ cycloalkyl that is fully saturated. In certain embodiments, $R^4$ is an optionally substituted $C_1$-$C_8$ alkyl or an optionally substituted $C_3$-$C_8$ cycloalkyl that is not fully saturated. In certain such embodiments, $R^4$ is selected from an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^4$ is selected from an optionally substituted methyl, ethyl propyl isopropyl, butyl, sec-butyl, and tert-butyl. In certain embodiments, $R^4$ is methyl. In certain embodiments, $R^4$ is trifluoromethyl. In certain of the embodiments where $R^4$ is a halogen, $R^4$ is F, Br, or Cl.

In certain embodiments, $R^5$ is selected from hydrogen, $OR^{10}$, $SR^{10}$, $NHR^{11}$, F, and $CO_2H$.

In certain embodiments, $R^6$ is selected from hydrogen, $OR^{12}$, $NR^{12}R^{13}$, $N=R^{12}$, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_3$-$C_8$ heterocycle, an optionally substituted an optionally substituted $C_6$-$C_{10}$ aryl, and an optionally substituted an optionally substituted $C_3$-$C_{10}$ heteroaryl. In certain embodiments, $R^6$ is an optionally substituted $C_1$-$C_8$ alkyl or an optionally substituted $C_3$-$C_8$ cycloalkyl that is fully saturated. In certain embodiments, $R^6$ is an optionally substituted $C_1$-$C_8$ alkyl or an optionally substituted $C_3$-$C_8$ cycloalkyl that is not fully saturated. In certain such embodiments, $R^6$ is selected from an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^6$ is selected from an optionally substituted methyl, ethyl propyl isopropyl, butyl, sec-butyl, and tert-butyl. In certain embodiments, $R^6$ is methyl. In certain embodiments, $R^6$ is trifluoromethyl. In certain of the embodiments where $R^6$ is a halogen, $R^6$ is F, Br, or Cl. In certain embodiments, $R^6$ is a ring. In certain embodiments, $R^6$ is a non-aromatic ring.

In certain embodiments, $R^7$ is selected from hydrogen, $(CH_2)_m R^{14}$, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_3$-$C_8$ heterocycle, an optionally substituted an optionally substituted $C_6$-$C_{10}$ aryl, and an optionally substituted an optionally substituted $C_3$-$C_{10}$ heteroaryl. In certain embodiments, $R^7$ is an optionally substituted $C_1$-$C_8$ alkyl or an optionally substituted $C_3$-$C_8$ cycloalkyl that is fully saturated. In certain embodiments, $R^7$ is an optionally substituted $C_1$-$C_8$ alkyl or an optionally substituted $C_3$-$C_8$ cycloalkyl that is not fully saturated. In certain such embodiments, $R^7$ is selected from an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^7$ is selected from an optionally substituted methyl, ethyl propyl isopropyl, butyl, sec-butyl, and tert-butyl. In certain embodiments, $R^7$ is methyl. In certain embodiments, $R^7$ is trifluoromethyl. In certain of the embodiments where $R^7$ is a halogen, $R^7$ is F, Br, or Cl. In certain embodiments, $R^7$ is a ring. In certain embodiments, $R^7$ is a non-aromatic ring.

In certain embodiments, $R^{10}$ is selected from hydrogen, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_3$-$C_8$ heterocycle, an optionally substituted an optionally substituted $C_6$-$C_{10}$ aryl, and an optionally substituted an optionally substituted $C_3$-$C_{10}$ heteroaryl. In certain embodiments, $R^{10}$ is an optionally substituted $C_1$-$C_8$ alkyl or an optionally substituted $C_3$-$C_8$ cycloalkyl that is fully saturated. In certain embodiments, $R^{10}$ is an optionally substituted $C_1$-$C_8$ alkyl or an optionally substituted $C_3$-$C_8$ cycloalkyl that is not fully saturated. In certain such embodiments, $R^{10}$ is selected from an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{10}$ is selected from an optionally substituted methyl, ethyl propyl isopropyl, butyl, sec-butyl, and tert-butyl. In certain embodiments, $R^{10}$ is methyl. In certain embodiments, $R^{10}$ is trifluoromethyl. In certain of the embodiments where $R^{10}$ is a halogen, $R^{10}$ is F, Br, or Cl.

In certain embodiments, $R^{11}$ is selected from hydrogen, $SO_2R^{15}$, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_3$-$C_8$ heterocycle, an optionally substituted an optionally substituted $C_6$-$C_{10}$ aryl, and an optionally substituted an optionally substituted $C_3$-$C_{10}$ heteroaryl. In certain embodiments, $R^{11}$ is an optionally substituted $C_1$-$C_8$ alkyl or an optionally substituted $C_3$-$C_8$ cycloalkyl that is fully saturated. In certain embodiments, $R^{11}$ is an optionally substituted $C_1$-$C_8$ alkyl or an optionally substituted $C_3$-$C_8$ cycloalkyl that is not fully saturated. In certain such embodiments, $R^{11}$ is selected from an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^1$ is selected from an optionally substituted methyl, ethyl propyl isopropyl, butyl, sec-butyl, and tert-butyl. In certain embodiments, $R^{11}$ is methyl. In certain embodiments, $R^{11}$ is trifluoromethyl. In certain of the embodiments where $R^{11}$ is a halogen, $R^{11}$ is F, Br, or Cl.

In certain embodiments, $R^{12}$ and $R^{13}$ are each independently selected from hydrogen, a halogen, $(CH_2)_m R^{14}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_3$-$C_8$ heterocycle, an optionally substituted $C_6$-$C_{10}$ aryl, and an optionally substituted $C_3$-$C_{10}$ heteroaryl. In certain embodiments, $R^{12}$ and/or $R^{13}$ is an optionally substituted $C_1$-$C_8$ alkyl or an optionally substituted $C_3$-$C_8$ cycloalkyl that is fully saturated. In certain embodiments, $R^{12}$ and/or R13 is an optionally substituted $C_1$-$C_8$ alkyl or an optionally substituted $C_3$-$C_8$ cycloalkyl that is not fully saturated. In certain such embodiments, $R^{12}$ and/or $R^{13}$ is selected from an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{12}$ and/or $R^{13}$ is selected from an optionally substituted methyl, ethyl propyl, isopropyl, butyl, sec-butyl, and tert-butyl. In certain embodiments, $R^{12}$ and/or $R^{13}$ is methyl. In certain embodiments, $R^{12}$ and/or $R^{13}$ is trifluoromethyl. In certain of the embodiments where $R^{12}$ and/or $R^{13}$ is a halogen, $R^{12}$ and/or $R^{13}$ is F or Cl. In certain embodiments, $R^{12}$ is methyl. In certain embodiments $R^{13}$ is methyl. In certain embodiments, $R^{12}$ is methyl and $R^{13}$ is methyl. In certain embodiments, at least one of $R^{12}$ and $R^{13}$ is not methyl. In certain embodiments, at least one of $R^{12}$ and $R^{13}$ is not hydrogen. In certain embodiments, if $R^{12}$ is hydrogen, then $R^{13}$ is not methyl.

In certain embodiments, $R^{12}$ and $R^{13}$ together form an optionally substituted $C_2$-$C_6$ alkene. In certain embodiments, $R^{12}$ and $R^{13}$ together form an optionally substituted $C_2$-$C_6$ alkynyl. In certain embodiments, R12 and $R^{13}$ are linked together, resulting in a ring formed by $R^{12}$, $R^{13}$, the carbon atom to which both $R^{12}$ and $R^{13}$ are bound, and the linker. In certain embodiments, the linker is selected from an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl.

In certain embodiments, $R^{14}$ is selected from a hydrogen, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_3$-$C_8$ heterocycle, an optionally substituted $C_6$-$C_{10}$ aryl, and an optionally substituted $C_3$-$C_{10}$ heteroaryl. In certain embodiments, $R^{14}$ is an optionally substituted $C_1$-$C_8$ alkyl or an optionally substituted $C_3$-$C_8$ cycloalkyl that is fully saturated. In certain embodiments, $R^{14}$ is an optionally substituted $C_1$-$C_8$ alkyl or an optionally substituted $C_3$-$C_8$ cycloalkyl that is not fully saturated. In certain such embodiments, $R^{14}$ is selected from an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{14}$ is selected from an optionally substituted methyl, ethyl propyl isopropyl, butyl, sec-butyl, and tert-butyl. In certain embodiments, $R^{14}$ is methyl. In certain embodiments, $R^{14}$ is trifluoromethyl. In certain of the embodiments where $R^{14}$ is a halogen, $R^{14}$ is F, Br, or Cl.

In certain embodiments, $R^{15}$ is selected from a hydrogen, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_3$-$C_8$ heterocycle, an optionally substituted $C_6$-$C_{10}$ aryl, and an optionally substituted $C_3$-$C_{10}$ heteroaryl. In certain embodiments, $R^{15}$ is an optionally substituted $C_1$-$C_8$ alkyl or an optionally substituted $C_3$-$C_8$ cycloalkyl that is fully saturated. In certain embodiments, $R^{15}$ is an optionally substituted $C_1$-$C_8$ alkyl or an optionally substituted $C_3$-$C_8$ cycloalkyl that is not fully saturated. In certain such embodiments, $R^{15}$ is selected from an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{15}$ is selected from an optionally substituted methyl, ethyl propyl isopropyl, butyl, sec-butyl, and tert-butyl. In certain embodiments, $R^{15}$ is methyl. In certain embodiments, $R^{15}$ is trifluoromethyl. In certain of the embodiments where $R^{15}$ is a halogen, $R^{15}$ is F, Br, or Cl.

In certain embodiments, Z is selected from a 2-5 atom spacer. In certain such embodiments, that 2-5 atom spacer is selected from an optionally substituted $C_6$-$C_{10}$ aryl and an optionally substituted $C_1$-$C_{10}$ heteroaryl. In certain embodiments, Z is selected from a 1-5 atom spacer. In certain such embodiments, that 1-5 atom spacer is selected from an optionally substituted $C_1$-$C_6$ alkyl, an optionally substituted $C_1$-$C_6$ heteroalkyl an optionally substituted $C_1$-$C_6$ haloalkyl, an optionally substituted $C_2$-$C_6$ alkenyl, an optionally substituted $C_2$-$C_6$ heteroalkenyl, an optionally substituted $C_2$-$C_6$ haloalkenyl, an optionally substituted $C_2$-$C_6$ alkynyl, an optionally substituted $C_2$-$C_6$ heteroalkynyl, O, S, and NH. For example, in certain embodiments, Z is an aryl or heteroaryl ring wherein the portion of the compound comprising $R^1$, $R^2$, and $R^3$ is bound to the ring and the portion comprising $R^4$ and $R^5$ are bound to the ring, where those portions are either meta, ortho or para to one another.

In certain embodiments, Z is selected from:

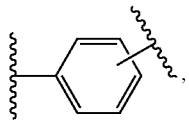 , 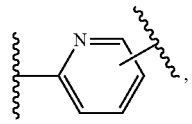 ,

-continued

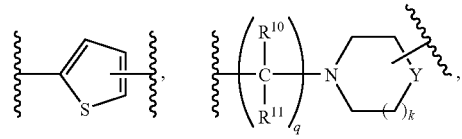

—$(CR^2R^3)_jO$—, and —$(CR^{10}R^{11})_qNR^{15}$—. In certain such embodiments, Y is selected from O, S, $NR^{10}$, and $CH_2$.

In certain embodiments, m is 0, 1, 2, or 3. In certain embodiments, n is 0, 1, 2, or 3. In certain embodiments, j is 1, 2, or 3. In certain embodiments, k is 0 or 1. In certain embodiments, q is 0, 1, or 2.

In certain embodiments, if $R_5$ is OH and $R^1$ is selected from $CO_2R^{10}$, $CONR^{10}R^{11}$, $SO_3R^{10}$, a tetrazole, and $NHSO_2R^{15}$, then at least one of $R^2$ and $R^3$ is not hydrogen.

In certain embodiments, if $R_5$ is OH and $R^1$ is selected from $CO_2R^{10}$, $CONR^{10}R^{11}$, $SO_3R^{10}$, a tetrazole, and $NHSO_2R^{15}$, then n is 1.

In certain embodiments, if $R_5$ is OH and $R^1$ is selected from $CO_2R^{10}$, $CONR^{10}R^{11}$, $SO_3R^{10}$, a tetrazole, and $NHSO_2R^{15}$, then Z is selected from an optionally substituted $C_6$-$C_{10}$ aryl, an optionally substituted $C_1$-$C_{10}$ heteroaryl, an optionally substituted $C_1$-$C_6$ non-straight-chain-alkoxy-heteroalkyl, and an optionally substituted $C_2$-$C_6$ heteroalkenyl.

In certain embodiments, if $R^5$ is OH and $R^1$ is selected from $CO_2R^{10}$, $CONR^{10}R^{11}$, $SO_3R^1$, a tetrazole, and $NHSO_2R^{15}$, then at least one of $R^2$ and $R^3$ is not hydrogen, and n is 1, and Z is selected from an optionally substituted $C_6$-$C_{10}$ aryl, an optionally substituted $C_1$-$C_{10}$ heteroaryl, an optionally substituted $C_1$-$C_6$ non-straight-chain-alkoxy-heteroalkyl, and an optionally substituted $C_2$-$C_6$ heteroalkenyl.

In certain embodiments, if $R^5$ is OH and $R^1$ is $CO_2R^1$, and Z is an aryl or heteroaryl, then at least one of $R^2$ and $R^3$ is not hydrogen or null.

In certain embodiments, if $R^5$ is OH and $R^1$ is selected from $CO_2R^{10}$, $CONR^{10}R^{11}$, $SO_3R^{10}$, a tetrazole, and $NHSO2R^{15}$, and Z is an aryl or heteroaryl, then n is 1.

In certain embodiments, if $R^5$ is OH, and $R^1$ is

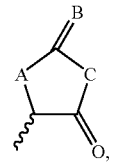

wherein A, B, and C are each independently selected from O, S, and N, and Z is an aryl or heteroaryl, then neither $R^2$ nor $R^3$ is not null.

In embodiments in which two or more of a particular group are present, the identities of those two or more particular groups are selected independently and, thus, may be the same or different from one another. For example, certain compounds of the invention comprise two or more $R^{10}$ groups. The identities of those two or more $R^{10}$ groups are each selected independently. Thus, in certain embodiments, those $R^{10}$ groups are all the same as one another; in certain embodiments, those $R^{10}$ groups are all different from one another; and in certain embodiments, some of those $R^{10}$ groups are the same as one another and some are different from one another. This independent selection applies to any group that is present in a compound more than once.

In certain embodiments, a compound of Formula I or Formula II is a selective TPO modulator. In certain embodiments, a compound of Formula I or Formula II is a selective TPO receptor agonist. In certain embodiments, a compound of Formula I or Formula II is a selective TPO receptor antagonist. In certain embodiments, a compound of Formula I or Formula II is a selective TPO receptor partial agonist. In certain embodiments, a compound of Formula I or Formula II is a tissue-specific selective TPO modulator. In certain embodiments, a compound of Formula I or Formula II is a selective TPO receptor binding compound. In certain embodiments, a compound of Formula I or Formula II is a TPO mimic.

In certain embodiments, the invention provides compounds selected from:

(±)-2-(3'- {N'-[1-(3,4-Dimethylphenyl)-3-methyl-5-oxo-1,5-dihydro-pyrazol-4-ylidene]-hydrazino}-2'-hydroxy-biphenyl-3-yl)-propionic acid (Compound 101);

2-(5'-Chloro-3'-{N'-[1-(3,4-dimethyl-phenyl)-3-methyl-5-oxo-1,5-dihydro-pyrazol-4-ylidene]-hydrazino}-2'-hydroxy-biphenyl-3-yl)-2-methyl-propionic acid (Compound 102);

(±)-2-(3'-{N'-[1-(3,4-Dimethylphenyl)-3-methyl-5-oxo-1,5-dihydro-pyrazol-4-ylidene]-hydrazino}-2'-hydroxy-biphenyl-3-yl)-3-phenylpropionic acid (Compound 103);

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-3-yl)-butyric acid (Compound 104);

(±)-2-(3'-{N'-[1-(3,4-Dimethylphenyl)-3-methyl-5-oxo-1,5-dihydro-pyrazol-4-ylidene]-hydrazino}-2'-hydroxy-biphenyl-4-yl)-propionic acid (Compound 105);

(±)-2-(3'-{N'-[1-(3,4-Dimethylphenyl)-3-methyl-5-oxo-1,5-dihydro-pyrazol-4-ylidene]-hydrazino}-2'-hydroxy-biphenyl-4-yl)-thiopropionic acid (Compound 106);

(±)-2-(3'-{N'-[1-(3,4-Dimethylphenyl)-3-methyl-5-oxo-1,5-dihydro-pyrazol-4-ylidene]-hydrazino}-5'-fluoro-2'-hydroxy-biphenyl-4-yl)-propionic acid (Compound 107);

(±)-2-(3'-{N'-[1-(3,4-Dimethylphenyl)-3-methyl-5-oxo-1,5-dihydro-pyrazol-4-ylidene]-hydrazino}-biphenyl-2,3'-dicarboxylic acid (Compound 108);

(±)-2-(3'-{N'-[1-(3,4-Dimethylphenyl)-3-methyl-5-oxo-1,5-dihydro-pyrazol-4-ylidene]-hydrazino}-2'-hydroxy-5'-methyl-biphenyl-4-yl)-propionic acid (Compound 109);

(±)-2-(3'-{N'-[1-(3,4-Dimethylphenyl)-3-methyl-5-oxo-1,5-dihydro-pyrazol-4-ylidene]-hydrazino}-2'-hydroxy-biphenyl-4-yl)-2-methyl-propionic acid (Compound 110);

(±)-2-(3'-{N'-[1-(3,4-Dimethylphenyl)-3-methyl-5-oxo-1,5-dihydro-pyrazol-4-ylidene]-hydrazino}-2'-hydroxy-biphenyl-4-yl)-hexanoic acid (Compound 111);

(±)-2-(3'-{N'-[1-(3,4-Dimethylphenyl)-3-methyl-5-oxo-1,5-dihydro-pyrazol-4-ylidene]-hydrazino}-2'-hydroxy-biphenyl-4-yl)-3-methyl-butyric acid (Compound 112);

(−)-2-(S)-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionic acid (Compound 113);

(+)-2-(R)-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionic acid (Compound 114);

(3'-{N'-[1-(3,4-Dimethyl-phenyl)-3-methyl-5-oxo-1,5-dihydro-pyrazol-4-ylidene]-hydrazino}-2'-hydroxy-biphenyl-4-yloxy)-acetic acid (Compound 115);

(±)-2-(3'-{N'-[1-(3,4-Dimethyl-phenyl)-3-methyl-5-oxo-1,5-dihydro-pyrazol-4-ylidene]-hydrazino}-5'-fluoro-2'-hydroxy-biphenyl-3-yl)-propionic acid (Compound 116);

(±)-{[2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionyl]-methyl-amino}acetic acid (Compound 117);

(±)-{[2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionyl]-methyl-amino}-acetic acid ethyl ester (Compound 118);

(±)-4-({5-Chloro-2-hydroxy-4'-[1-(1H-tetrazol-5-yl)-ethyl]-biphenyl-3-yl}-hydrazono)-2-(3,4-dimethyl-phenyl)-5-methyl-2,4-dihydro-pyrazol-3-one (Compound 119);

(±)-2-(3,4-Dimethyl-phenyl)-4-({2-hydroxy-4'-[1-(1H-tetrazol-5-yl)-ethyl]-biphenyl-3-yl}-hydrazono)-5-methyl-2,4-dihydro-pyrazol-3-one (Compound 120);

(±)-2-(2'-Hydroxy-[3'-{N-3-methyl-5-oxo-1-(4-propyl-phenyl)-1,5-dihydro-pyrazol-4-ylidene]-hydrazino}-biphenyl-4-yl)-propionic acid (Compound 121);

3'-{N'-[1-(3,4-Dimethyl-phenyl)-3-methyl-5-oxo-1,5-dihydro-pyrazol-4-ylidene]-hydrazino}-2'-fluoro-biphenyl-3-carboxylic acid (Compound 122);

2-(3'-{N'-[1-(3,4-Dimethyl-phenyl)-3-methyl-5-oxo-1,5-dihydro-pyrazol-4-ylidene]-hydrazino}-2'-hydroxy-5'-methyl-biphenyl-3-yloxy)-2-methyl-propionic acid (Compound 123);

[(3'-{N'-[1-(3,4-Dimethyl-phenyl)-3-methyl-5-oxo-1,5-dihydro-pyrazol-4-ylidene]-hydrazino}-2'-hydroxy-biphenyl-3-carbonyl)-amino]-acetic acid (Compound 124);

[(3'-{N'-[1-(3,4-Dimethyl-phenyl)-3-methyl-5-oxo-1,5-dihydro-pyrazol-4-ylidene]-hydrazino}-2'-hydroxy-biphenyl-3-carbonyl)-amino]-acetic acid ethyl ester (Compound 125);

(±)-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-methoxy-acetic acid (Compound 126);

(±)-2-(5'-Chloro-3'-{N'-[1-(3,4-dimethyl-phenyl)-3-methyl-5-oxo-1,5-dihydro-pyrazol-4-ylidene]-hydrazino}-2'-hydroxy-biphenyl-3-yloxy)-butyric acid (Compound 127);

3'-{N'-[1-(3,4-Dimethyl-phenyl)-3-methyl-5-oxo -1,5-dihydro-pyrazol-4-ylidene]-hydrazino}-2'-methoxy-biphenyl-3-carboxylic acid (Compound 128);

(±)-2-(3'- {N'-[1-(3,4-Dimethyl-phenyl)-3-methyl-5-oxo-1,5-dihydro-pyrazol-4-ylidene]-hydrazino}-2'-hydroxy-biphenyl-4-yl)-butyric acid (Compound 129);

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yloxy)-propionic acid (Compound 130);

2-(5'-Chloro-3'-{N'-[1-(3,5-dimethyl-phenyl)-3-methyl-5-oxo-1,5-dihydro-pyrazol-4-ylidene]-hydrazino}-2'-hydroxy-biphenyl-3-yl)-2-methyl-propionic acid (Compound 131);

and a pharmaceutically acceptable salt, ester, amide, or prodrug of any of those compounds. In certain embodiments, such compounds are selective TPO modulators.

Certain compounds of the present inventions may exist as stereoisomers including optical isomers. The present disclosure is intended to include all stereoisomers and both the racemic mixtures of such stereoisomers as well as the individual enantiomers that may be separated according to methods that are known in the art or that may be excluded by synthesis schemes known in the art designed to yield predominantly one enantiomer relative to another.

Certain Synthesis Methods

In certain embodiments, certain compounds of the present invention can by synthesized using the following Schemes.

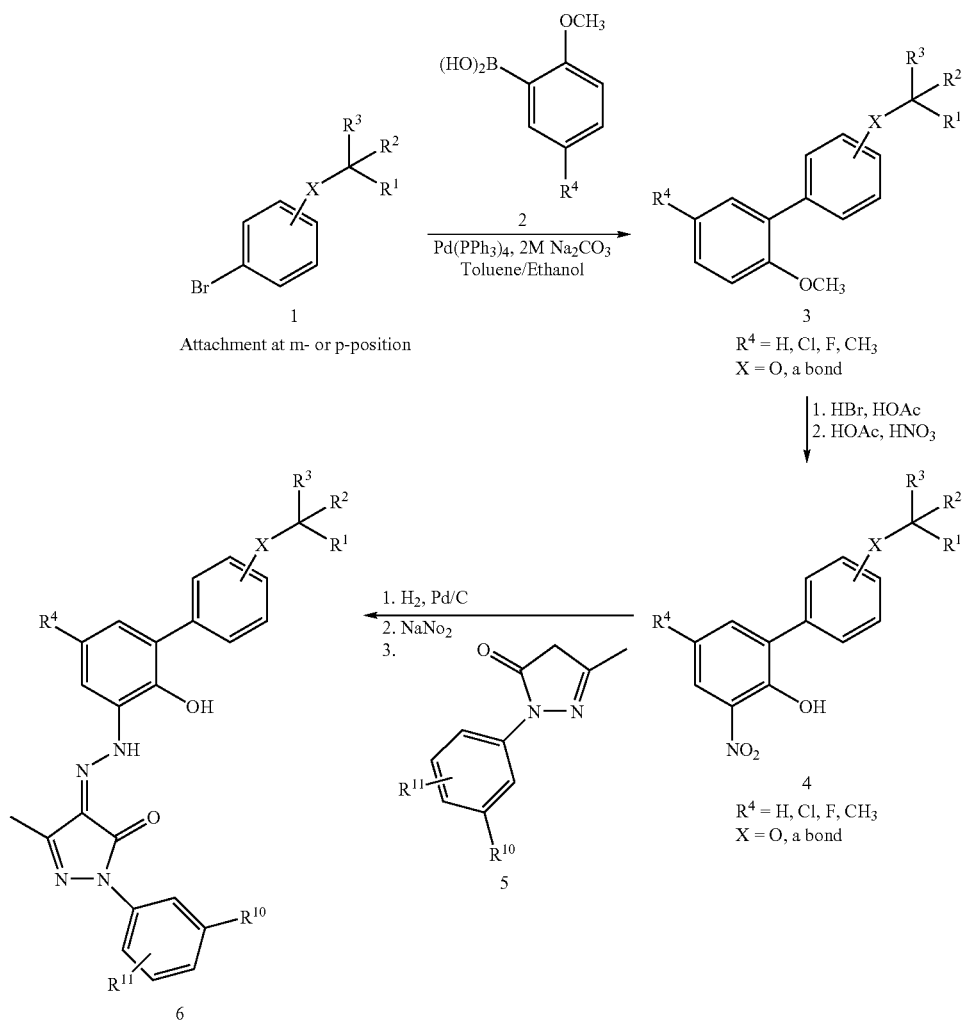

The process of Scheme I is a multi-step synthetic sequence that commences with the palladium catalyzed cross-coupling of a phenylboronic acid of structure 2 and an aryl bromide, such as compounds of structure 1 to produce the biphenyl of structure 3. Methyl ether deproctection followed by nitration of structure 3 give compounds of structure 4. Hydrogenation and diazotization of structure 4 followed by coupling with pyrazinone 5 to give the final product of structure 6.

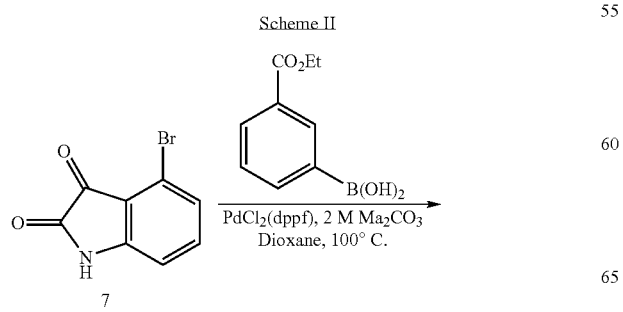

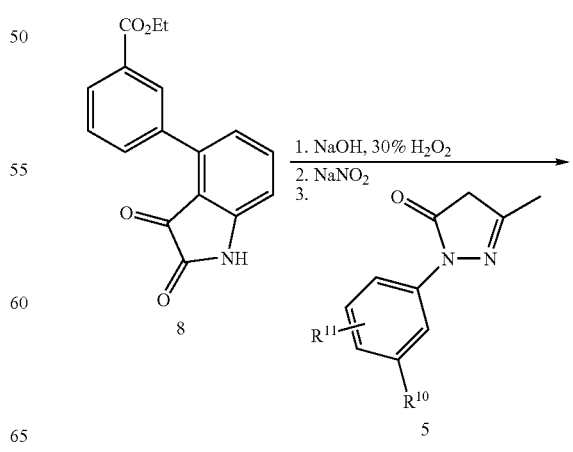

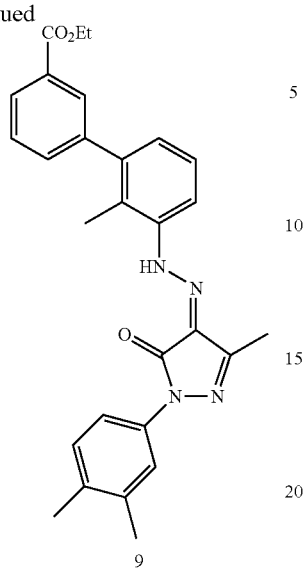
The process of Scheme II is a multi-step synthetic sequence that commences with the palladium catalyzed cross-coupling of a bromo-isatin such as structure 7 with a phenylboronic acid to give intermediate 8. This is then followed by subsequent isatin ring-opening, diazotization, and coupling with a pyrazinone 5 to give the final product of structure 9.
Scheme III
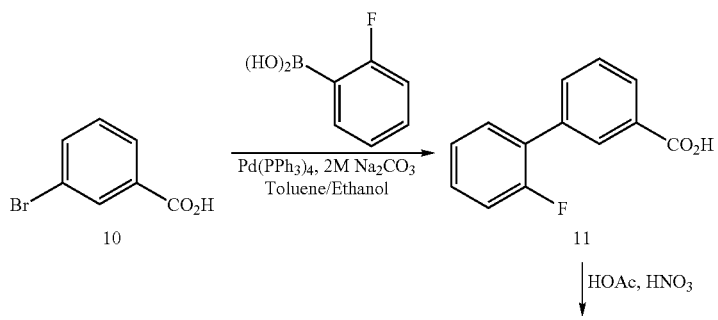
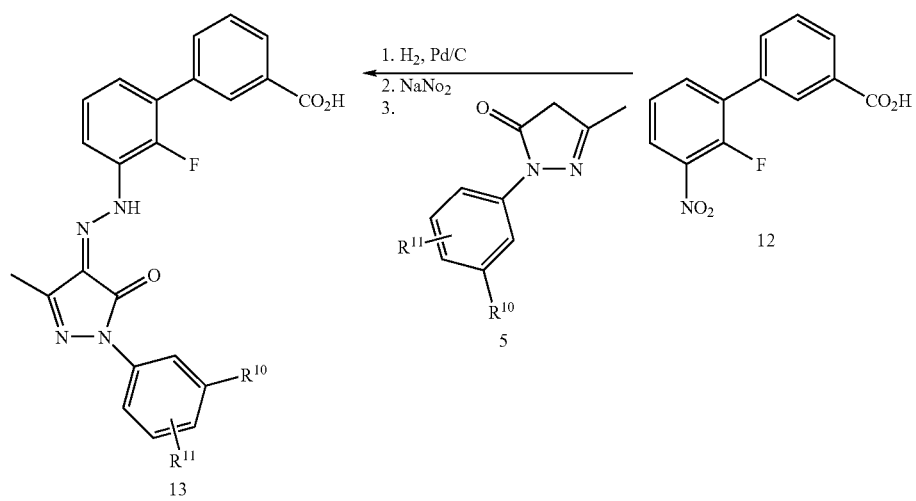

The process of Scheme III is a multi-step synthetic sequence that commences with the palladium catalyzed cross-coupling of an aryl bromide 10 and a phenylboronic acid to produce the biphenyl of structure 11. Nitration of structure 11 gives compound 11. Hydrogenation and diazotization of structure 12 followed by coupling with pyrazinone 5 to give the final product of structure 13.

One of skill in the art will recognize that analogous synthesis schemes may be used to synthesize similar compounds. One of skill will recognize that compounds of the present invention may be synthesized using other synthesis schemes.

In certain embodiments, the invention provides a salt corresponding to any of the compounds provided herein. In certain embodiments, the invention provides a salt corresponding to a selective TPO modulator. In certain embodiments, the invention provides a salt corresponding to a selective TPO receptor binding agent. In certain embodiments, a salt is obtained by reacting a compound with an inorganic acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

In certain embodiments, one or more carbon atoms of a compound of the present invention are replaced with silicon. See e.g., WO 03/037905A1; Tacke and Zilch, Endeavour, New Series, 10, 191-197 (1986); Bains and Tacke, Curr. Opin. Drug Discov Devel. Jul: 6(4):526-43(2003), all of which are incorporated herein by reference in their entirety. In certain embodiments, compounds of the present invention comprising one or more silicon atoms possess certain desired properties, including, but not limited to, greater stability and/or longer half-life in a patient, when compared to the same compound in which none of the carbon atoms have been replaced with a silicon atom.

Certain Assays

In certain embodiments, assays may be used to determine the level of TPO modulating activity of the compounds of the present invention. For example, the potency of the compounds of the present invention as selective TPO modulators may be determined in a luciferase assay, such as those described in Lamb, et al., Nucleic Acids Research, 23: 3283-3289(1995) and/or Seidel et al., Proc. Nat. Acad. Sci. USA; 92: 3041-3045 (1995), both of which are incorporated herein by reference in their entirety.

In vitro proliferation and/or differentiation assays may also be used, such as those described by Bartley et al., Cell, 77: 1117-1124 (1994) and/or Cwirla, et al., Science, 276: 1696-1699 (1997), both of which are incorporated herein by reference in their entirety.

Certain Pharmaceutical Agents

In certain embodiments, at least one selective TPO modulator, or pharmaceutically acceptable salt, ester, amide, and/or prodrug thereof, either alone or combined with one or more pharmaceutically acceptable carriers, forms a pharmaceutical agent. Techniques for formulation and administration of compounds of the present invention may be found for example, in "Remington's Pharmaceutical Sciences," Mack Publishing Co., Easton, Pa., 18th edition, 1990, which is incorporated herein by reference in its entirety.

In certain embodiments, a pharmaceutical agent comprising one or more compounds of the present invention is prepared using known techniques, including, but not limited to mixing, dissolving, granulating, dragee-making, levigating, emulsifying, encapsulating, entrapping or tabletting processes.

In certain embodiments, a pharmaceutical agent comprising one or more compounds of the present invention is a liquid (e.g., a suspension, elixir and/or solution). In certain of such embodiments, a liquid pharmaceutical agent comprising one or more compounds of the present invention is prepared using ingredients known in the art, including, but not limited to, water, glycols, oils, alcohols, flavoring agents, preservatives, and coloring agents.

In certain embodiments, a pharmaceutical agent comprising one or more compounds of the present invention is a solid (e.g, a powder, tablet, and/or capsule). In certain of such embodiments, a solid pharmaceutical agent comprising one or more compounds of the present invention is prepared using ingredients known in the art, including, but not limited to, starches, sugars, diluents, granulating agents, lubricants, binders, and disintegrating agents.

In certain embodiments, a pharmaceutical agent comprising one or more compounds of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical agent comprising one or more compounds of the present invention comprises a delivery system. Examples of delivery systems include, but are not limited to, liposomes and emulsions. Certain delivery systems are useful for preparing certain pharmaceutical agents including those comprising hydrophobic compounds. In certain embodiments, certain organic solvents such as dimethylsulfoxide are used.

In certain embodiments, a pharmaceutical agent comprising one or more compounds of the present invention comprises one or more tissue-specific delivery molecules designed to deliver the pharmaceutical agent to specific tissues or cell types. For example, in certain embodiments, pharmaceutical agents include liposomes coated with a tissue-specific antibody.

In certain embodiments, a pharmaceutical agent comprising one or more compounds of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical agent comprising one or more compounds of the present invention comprises a sustained-release system. A non-limiting example of such a sustained-release system is a semi-permeable matrix of solid hydrophobic polymers. In certain embodiments, sustained-release systems may, depending on their chemical nature, release compounds over a period of hours, days, weeks or months.

Certain compounds used in pharmaceutical agent of the present invention may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc.

In certain embodiments, a pharmaceutical agent comprising one or more compounds of the present invention comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, a pharmaceutical agent comprising one or more compounds of the present invention is formulated as a prodrug. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain instances the carboxylic acid containing compound is the corresponding active form. In certain embodiments, a prodrug comprises a short peptide (polyaminoacid) bound to an acid group. In certain of such embodiments, the peptide is metabolized to form the corresponding active form.

In certain embodiments, a pharmaceutical agent comprising one or more compounds of the present invention is useful for treating a conditions or disorder in a mammalian, and particularly in a human patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical agents may be injected directly in the area of desired effect (e.g., in the renal or cardiac area).

In certain embodiments, a pharmaceutical agent comprising one or more compounds of the present invention is administered in the form of a dosage unit (e.g., tablet, capsule, bolus, etc.). In certain embodiments, such dosage units comprise a selective TPO modulator in a dose from about 1 µg/kg of body weight to about 50 mg/kg of body weight. In certain embodiments, such dosage units comprise a selective TPO modulator in a dose from about 2 µg/kg of body weight to about 25 mg/kg of body weight. In certain embodiments, such dosage units comprise a selective TPO modulator in a dose from about 10 µg/kg of body weight to about 5 mg/kg of body weight. In certain embodiments, pharmaceutical agents are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical agent.

In certain embodiments, a pharmaceutical agent comprising a compound of the present invention is prepared for oral administration. In certain of such embodiments, a pharmaceutical agent is formulated by combining one or more compounds of the present invention with one or more pharmaceutically acceptable carriers. Certain of such carriers enable compounds of the invention to be formulated as tablets, pills, dragees, capsules, liquids, gels, syrups, slurries, suspensions and the like, for oral ingestion by a patient. In certain embodiments, pharmaceutical agents for oral use are obtained by mixing one or more compounds of the present invention and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical agents are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical agents for oral administration are push-fit capsules made of gelatin. Certain of such push-fit capsules comprise one or more compounds of the present invention in admixture with one or more filler such as lactose, binders such as starches, and/or lubricants such as talc or magnesium stearate and, optionally, stabilizers. In certain embodiments, pharmaceutical agents for oral administration are soft, sealed capsules made of gelatin and a plasticizer, such as glycerol or sorbitol. In certain soft capsules, one or more compounds of the present invention are be dissolved or suspended in suitable liquids, such as fatty oils, liquid paraffin, or liquid polyethylene glycols. In addition, stabilizers may be added.

In certain embodiments, pharmaceutical agents are prepared for buccal administration. Certain of such pharmaceutical agents are tablets or lozenges formulated in conventional manner.

In certain embodiments, a pharmaceutical agent is prepared for administration by injection (e.g., intravenous, subcutaneous, intramuscular, etc.). In certain of such embodiments, a pharmaceutical agent comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical agents for injection are presented in unit dosage form, e.g, in ampoules or in multi-dose containers. Certain pharmaceutical agents for injection are suspensions, solutions or emulsions in oily or aqueous vehicles, and may contain formulatory agents such as suspending, stabilizing and/or dispersing agents. Certain solvents suitable for use in pharmaceutical agents for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical agent is prepared for transmucosal administration. In certain of such embodiments penetrants appropriate to the barrier to be permeated are used in the formulation. Such penetrants are generally known in the art.

In certain embodiments, a pharmaceutical agent is prepared for administration by inhalation. Certain of such pharmaceutical agents for inhalation are prepared in the form of an aerosol spray in a pressurized pack or a nebulizer. Certain of such pharmaceutical agents comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a compound of the invention and a suitable powder base such as lactose or starch.

In certain embodiments, a pharmaceutical agent is prepared for rectal administration, such as a suppositories or retention enema. Certain of such pharmaceutical agents comprise known ingredients, such as cocoa butter and/or other glycerides.

In certain embodiments, a pharmaceutical agent is prepared for topical administration. Certain of such pharmaceutical agents comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, the formulation, route of administration and dosage for a pharmaceutical agent of the present invention can be chosen in view of a particular patient's condition. (See e.g., Fingl et al. 1975, in "The Pharmacological Basis of Therapeutics", Ch. 1 p. 1, which is incorporated herein by reference in its entirety). In certain embodiments, a pharmaceutical agent is administered as a single dose. In certain embodiments, a pharmaceutical agent is administered as a series of two or more doses administered over one or more days.

In certain embodiments, a pharmaceutical agent of the present invention is administered to a patient between about 0.1% and 500%, 5% and 200%, 10% and 100%, 15% and 85%, 25% and 75%, or 40% and 60% of an established human dosage. Where no human dosage is established, a suitable human dosage may be inferred from $ED_{50}$ or $ID_{50}$ values, or other appropriate values derived from in vitro or in vivo studies.

In certain embodiments, a daily dosage regimen for a patient comprises an oral dose of between 0.1 mg and 2000 mg, 5 mg and 1500 mg, 10 mg and 1000 mg, 20 mg and 500 mg, 30 mg and 200 mg, or 40 mg and 100 mg of a compound of the present invention. In certain embodiments, a daily dosage regimen is administered as a single daily dose. In certain embodiments, a daily dosage regimen is administered as two, three, four, or more than four doses.

In certain embodiments, a pharmaceutical agent of the present invention is administered by continuous intravenous infusion. In certain of such embodiments, from 0.1 mg to 500 mg of a composition of the present invention is administered per day.

In certain embodiments, a pharmaceutical agent of the invention is administered for a period of continuous therapy. For example, a pharmaceutical agent of the present invention may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration on compound in a patient. For example, in certain embodiments, dosage amount and interval between doses are adjusted to provide plasma concentration of a compound of the present invention at an amount sufficient to achieve a desired effect. In certain of such embodiments the plasma concentration is maintained above the minimal effective concentration (MEC). In certain embodiments, pharmaceutical agents of the present invention are administered with a dosage regimen designed to maintain a concentration above the MEC for 10-90% of the time, between 30-90% of the time, or between 50-90% of the time.

In certain embodiments in which a pharmaceutical agent is administered locally, the dosage regimen is adjusted to achieve a desired local concentration of a compound of the present invention.

In certain embodiments, a pharmaceutical agent may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

In certain embodiments, a pharmaceutical agent is in powder form for constitution with a suitable vehicle, e.g., sterile pyrogen-free water, before use.

Certain Combination Therapies

In certain embodiments, one or more pharmaceutical agents of the present invention are co-administered with one or more other pharmaceutical agents. In certain embodiments, such one or more other pharmaceutical agents are designed to treat the same disease or condition as the one or more pharmaceutical agents of the present invention. In certain embodiments, such one or more other pharmaceutical agents are designed to treat a different disease or condition as the one or more pharmaceutical agents of the present invention. In certain embodiments, such one or more other pharmaceutical agents are designed to treat an undesired effect of one or more pharmaceutical agents of the present invention. In certain embodiments, one or more pharmaceutical agents of the present invention are co-administered with another pharmaceutical agent to treat an undesired effect of that other pharmaceutical agent. In certain embodiments, one or more pharmaceutical agents of the present invention and one or more other pharmaceutical agents are administered at the same time. In certain embodiments, one or more pharmaceutical agents of the present invention and one or more other pharmaceutical agents are administered at the different times. In certain embodiments, one or more pharmaceutical agents of the present invention and one or more other pharmaceutical agents are prepared together in a single formulation. In certain embodiments, one or more pharmaceutical agents of the present invention and one or more other pharmaceutical agents are prepared separately.

Examples of pharmaceutical agents that may be co-administered with a pharmaceutical agent of the present invention include, but are not limited to, anti-cancer treatments, including, but not limited to, chemotherapy and radiation treatment; corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

Certain Indications

In certain embodiments, the invention provides methods of treating a patient comprising administering one or more compounds of the present invention. In certain embodiments, such patient suffers from thrombocytopenia. In certain such embodiments, thrombocytopenia results from chemotherapy and/or radiation treatment. In certain embodiments, thrombocytopenia results bone marrow failure resulting from bone marrow transplantation and/or aplastic anemia. In certain embodiments thrombocytopenia is idiopathic. In certain embodiments, one or more compounds of the present invention are administered to a patient to in conjunction with harvesting peripheral blood progenitor cells and/or in conjunction with platelet apheresis. Such administration may be done before, during, and/or after such harvesting.

In certain embodiments, one or more compounds of the present invention are administered to a patient who suffers from a condition affecting the nervous system, including, but are not limited to, diseases affecting the nervous system and injuries to the nervous system. Such diseases, include, but not limited to, amyotrophic lateral sclerosis, multiple sclerosis, and multiple dystrophy. Injury to the nervous system include, but are not limited to spinal cord injury or peripheral nerve damage, including, but not limited to, injury resulting from trauma or from stroke. In certain embodiments, one or more compounds of the present invention are used to promote growth and/or development of glial cells. Such glial cells may repair nerve cells. In certain embodiments, compounds of the present invention are used to treat psychological disorders, including, but not limited to, cognitive disorders.

EXAMPLES

The following examples, including experiments and results achieved, are provided for illustrative purposes only and are not to be construed as limiting the present invention.

Example 1

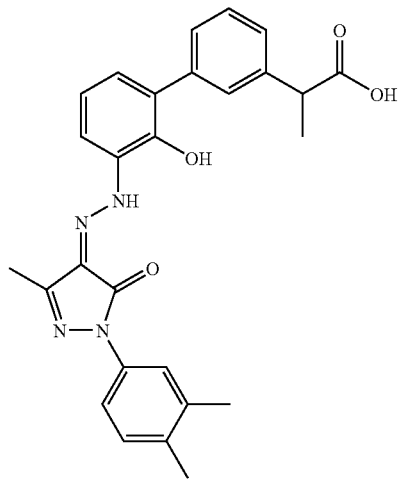

(±)-2-(3'-{N'-[1-(3,4-Dimethylphenyl)-3-methyl-5-oxo-1,5-dihydro-pyrazol-4-ylidene]-hydrazino}-2'-hydroxy-biphenyl-3-yl)-propionic acid (Compound 101) was prepared as described in Scheme I. $^1$H NMR (500 MHz, DMSO-d$_6$) δ 7.84 (s, 1H), 7.79 (d, J=7.0 Hz, 1H), 7.53 (s, 1H), 7.47 (d, J=7.5 Hz, 1H), 7.36 (t, J=7.0 Hz, 1H), 7.32 (d, J=5.5 Hz, 1H), 7.22 (d, J=7.5 Hz, 1H), 7.05 (d, J=8.5 Hz, 1H), 6.98 (d, J=5.0 Hz, 1H), 6.89 (t, J=6.6 Hz, 1H), 3.72 (q, J=7.0 Hz, 1H), 2.38 (s, 3H), 2.22 (s, 3H), 2.18 (s, 3H), 1.40 (d, J=7.0 Hz, 3H).

Example 2

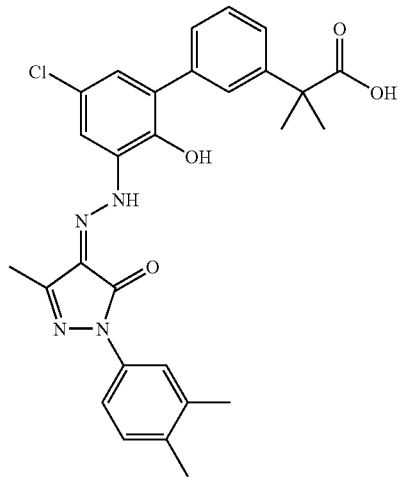

2-(5'-Chloro-3'-{N'-[1-(3,4-dimethyl-phenyl)-3-methyl-5-oxo-1,5-dihydro-pyrazol-4-ylidene]-hydrazino}-2'-hydroxy-biphenyl-3-yl)-2-methyl-propionic acid (Compound 102) was prepared as described in Scheme I. $^1$H NMR (500 MHz, DMSO-$d_6$) δ 7.84 (s, 1H), 7.79 (d, J=8.0 Hz, 1H), 7.58 (s, 1H), 7.48 (d, J=7.5 Hz, 1H), 7.41 (t, J=8.0 Hz, 1H), 7.34 (d, J=8.0 Hz, 1H), 7.29 (d, J=2.5 Hz, 1H), 7.08 (d, J=8.5 Hz, 1H), 6.96 (d, J=2.5 Hz, 1H), 2.40 (s, 3H), 2.24 (s, 3H), 2.20 (s, 3H), 1.54 (s, 6H).

Example 3

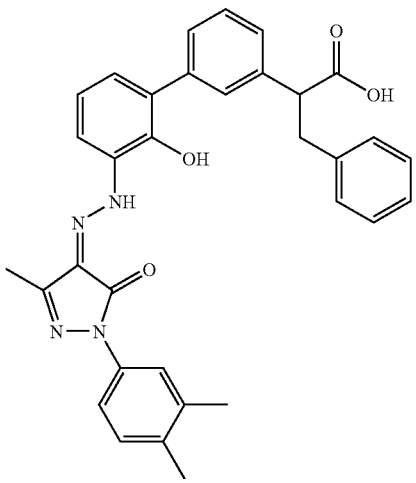

(±)-2-(3'-{N'-[1-(3,4-Dimethylphenyl)-3-methyl-5-oxo-1,5-dihydro-pyrazol-4-ylidene]-hydrazino}-2'-hydroxy-biphenyl-3-yl)-3-phenylpropionic acid (Compound 103) was prepared as described in Scheme I. $^1$H NMR (500 MHz, Methanol-$d_4$) δ 7.72 (dd, J=6.6, 2.5, Hz, 1H), 7.68 (d, J=2.0 Hz, 1H), 7.59 (dd, J=8.0, 2.0 Hz, 1H), 7.44 (s, 1H), 7.40-7.37 (m, 1H), 7.35 (t, J=8.0 Hz, 1H), 7.33-7.31 (m, 1H), 7.18-7.16 (m, 5H), 7.11-7.08 (m, 1H), 7.06-7.02 (m, 2H), 3.83 (t, J=8.0 Hz, 1H), 3.44 (dd, J=13.5, 8.0 Hz, 1H), 3.03 (dd, J=14.0, 7.5 Hz, 1H), 2.37 (s, 3H), 2.31 (s, 3H), 2.27 (s, 3H), 1.92 (s, 1H).

Example 4

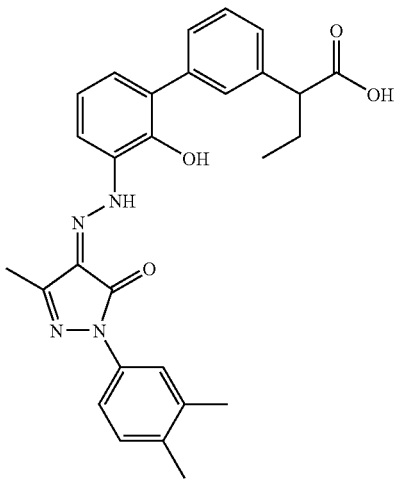

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-3-yl)-butyric acid (Compound 104) was prepared as described in Scheme I. $^1$H NMR (500 MHz, DMSO-$d_6$) δ 12.38 (s, 1H), 9.59 (s, 1H), 7.72 (s, 1H), 7.68 (dd, J=6.6, 2.0 Hz, 1H), 7.64 (dd, J=8.5, 2.0 Hz, 1H), 7.50 (s, 1H), 7.48-7.46 (m, 1H), 7.44 (t, J=7.5 Hz, 1H), 7.33-7.30 (m, 1H), 7.20 (d, J=9.0 Hz, 1H), 7.15-7.11 (m, 2H), 3.49 (t, J=7.5 Hz, 1H), 2.33 (s, 3H), 2.27 (s, 3H), 2.23 (s, 3H), 2.42-1.91 (m, 1H), 1.75-1.69 (m, 1H), 2.89 (t, J=7.5 Hz, 3H).

Example 5

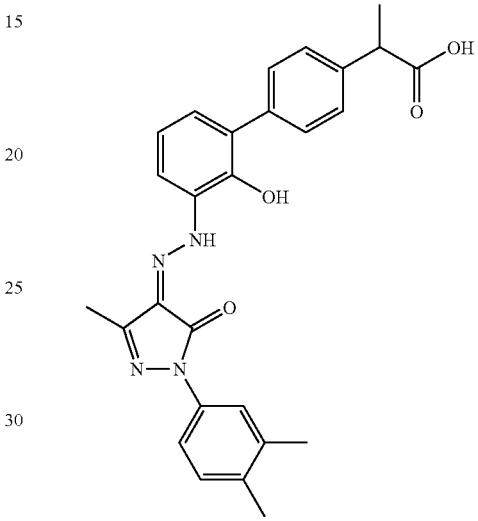

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionic acid (Compound 105) was prepared as described in Scheme I. $^1$H NMR (500 MHz, DMSO-$d_6$) δ 12.38 (s, 1H), 9.60 (s, 1H), 7.71 (d, J=2.5 Hz, 1H), 7.67 (dd, J=6.5, 3.5 Hz, 1H), 7.63 (dd, J=8.5, 2.5 Hz, 1H), 7.54 (d, J=8.5 Hz, 2H), 7.40 (d, J=8.0 Hz, 2H), 7.20 (d, J=8.0 Hz, 1H), 7.13-7.09 (m, 2H), 3.74 (q, J=7.5 Hz, 1H), 2.32 (s, 3H), 2.27 (s, 3H), 2.22 (s, 3H), 1.41 (d, J=7.5 Hz, 3H).

Example 6

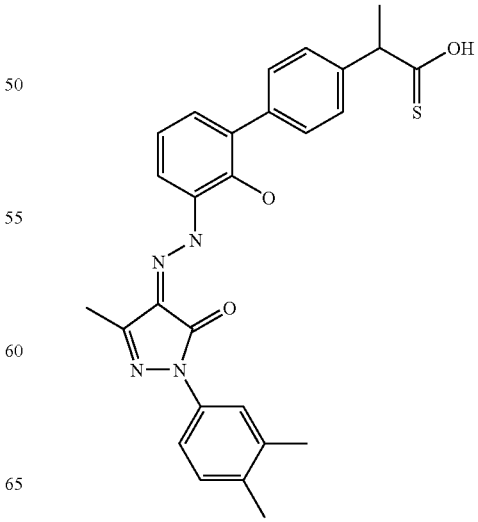

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-thiopropionic acid (Compound 106) was prepared as described in Scheme I. ¹H NMR (500 MHz, DMSO-d₆) δ 13.68 (s, 1H), 9.62 (s, 1H), 7.71 (d, J=2.5 Hz, 1H), 7.67 (dd, J=3.0 Hz, 1H), 7.63 (dd, J=8.5, 2.5 Hz, 1H), 7.54 (d, J=8.5 Hz, 2H), 7.44 (d, J=8.0 Hz, 2H), 7.20 (d, J=8.0 Hz, 1H), 7.13-7.09 (m, 2H), 4.15 (q, J=6.5 Hz, 1H), 2.32 (s, 3H), 2.26 (s, 3H), 2.22 (s, 3H), 1.46 (d, J=7.0 Hz, 3H).

Example 7

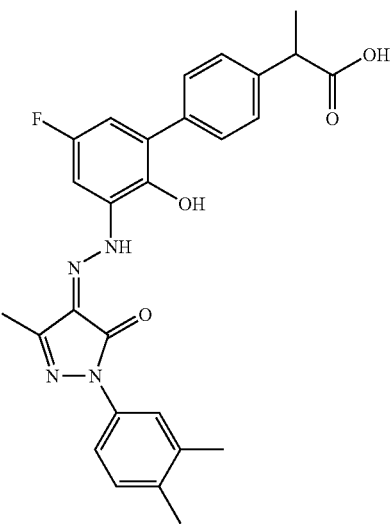

(±)-2-(3'-{N'-[1-(3,4-Dimethyl-phenyl)-3-methyl-5-oxo-1,5-dihydro-pyrazol-4-ylidene]-hydrazino}-5'-fluoro-2'-hydroxy-biphenyl-4-yl)-propionic acid (Compound 107) was prepared as described in Scheme I. ¹H NMR (500 MHz, DMSO-d₆) δ 9.53 (s, 1H), 7.69 (d, J=1.5 Hz, 1H), 7.62 (dd, J=8.0, 2.0 Hz, 1H), 7.58 (d, J=8.0 Hz, 2H), 7.45 (dd, J=9.0, 3.0 Hz, 1H), 7.41 (d, J=8.0 Hz, 2H), 7.21 (d, J=8.5 Hz, 1H), 6.98 (dd, J=9.0, 3.0 Hz, 1H), 3.75 (q, J=7.5 Hz, 1H), 2.33 (s, 3H), 2.27 (s, 3H), 2.23 (s, 3H), 1.41 (d, J=7.5 Hz, 3H).

Example 8

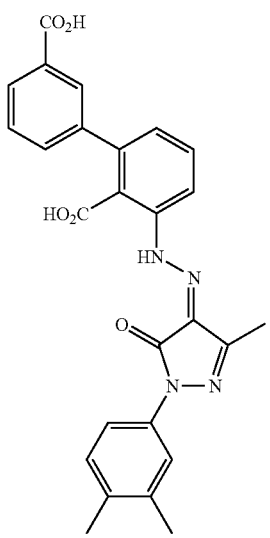

3-{N'-[1-(3,4-Dimethyl-phenyl)-3-methyl-5-oxo-1,5-dihydro-pyrazol-4-ylidene]-hydrazino}-biphenyl-2,3'-dicarboxylic acid (Compound 108) was prepared as described in Scheme II. ¹H NMR (500 MHz, Acetone-d₆) δ 8.10-8.06 (m, 2H), 7.77-7.68 (m, 4H), 7.60 (t, J=7.6 Hz, 1H), 7.30 (dd, J=7.8, 1.0 Hz, 1H), 7.19 (d, J=8.3 Hz, 1H), 2.36 (s, 3H), 2.30 (s, 3H), 2.26 (s, 3H).

Example 9

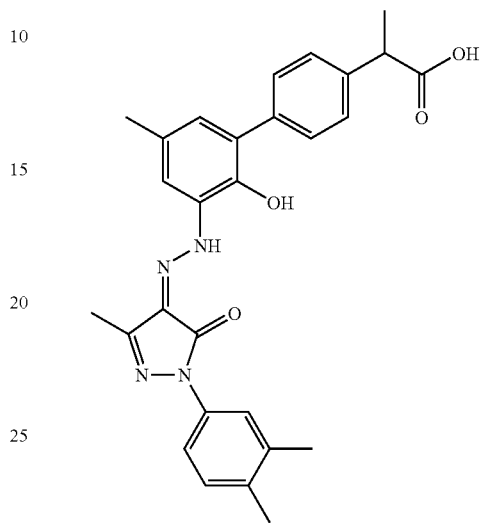

(±)-2-(3'-{N'-[1-(3,4-Dimethyl-phenyl)-3-methyl-5-oxo-1,5-dihydro-pyrazol-4-ylidene]-hydrazino}-2'-hydroxy-5'-methyl-biphenyl-4-yl)-propionic acid (Compound 109) was prepared as in Scheme I. ¹H NMR (500 MHz, DMSO-d₆) δ 13.74 (s, 1H), 12.36 (s, 1H), 9.34 (s, 1H), 7.71 (d, J=2.1 Hz, 1H), 7.63 (dd, J=8.2, 2.1 Hz, 1H), 7.53 (d, J=8.3 Hz, 2H), 7.49 (d, J=2.0 Hz, 1H), 7.39 (d, J=8.3 Hz, 2H), 7.20 (d, J=8.2 Hz, 1H), 6.95 (d, J=2.0 Hz, 1H), 3.74 (q, J=7.2 Hz, 1H), 2.33 (s, 6H), 2.27 (s, 3H), 2.23 (s, 3H), 1.41 (d, J=7.2Hz, 3H).

Example 10

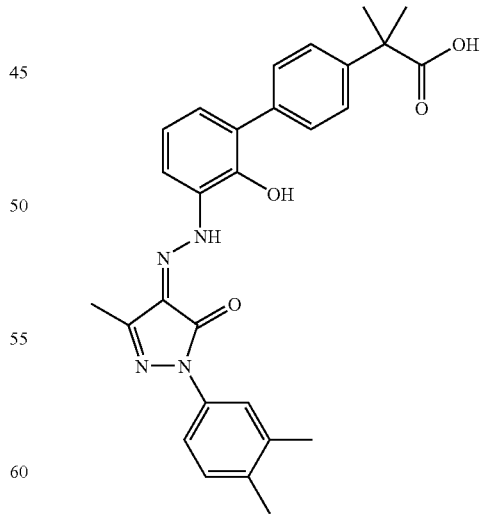

2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-2-methyl-propionic acid (Compound 110) was prepared as in Scheme I. ¹H NMR (500 MHz, DMSO-d₆) δ 13.73

(s, 1H), 12.40 (s, 1H), 9.61 (s, 1H), 7.71 (d, J=2.0 Hz, 1H), 7.68 (dd, J=6.7, 2.9 Hz, 1H), 7.63 (dd, J=8.3, 2.0 Hz, 1H), 7.56 (d, J=8.5 Hz, 2H), 7.46 (d, J=8.5 Hz, 2H), 7.20 (d, J=8.3 Hz, 1H), 7.14-7.10 (m, 2H), 2.33 (s, 3H), 2.27 (s, 3H), 2.23 (s, 3H), 1.53 (s, 6H).

Example 11

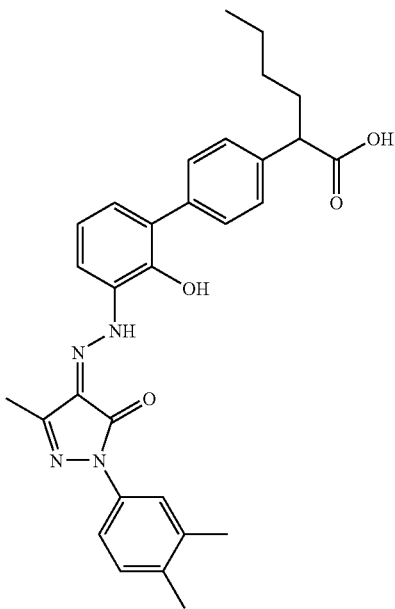

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-hexanoic acid (Compound 111) was prepared as in Scheme I. $^1$H NMR (500 MHz, DMSO-d$_6$) δ 13.73 (s, 1H), 12.34 (s, 1H), 9.60 (s, 1H), 7.71 (d, J=1.8 Hz, 1H), 7.67 (dd, J=6.8, 2.0 Hz, 1H), 7.63 (dd, J=8.2, 1.8 Hz, 1H), 7.54 (d, J=7.8 Hz, 2H), 7.40 (d, J=7.8 Hz, 2H), 7.20 (d, J=8.2 Hz, 1H), 7.14-7.08 (m, 2H), 3.54 (t, J=7.7 Hz, 2H), 2.32 (s, 3H), 2.26 (s, 3H), 2.22 (s, 3H), 1.99 (m, 1H), 1.68 (m, 1H), 1.31 (m, 2H), 1.21 (m, 2H), 0.86 (t, J=7.2 Hz, 3H).

Example 12

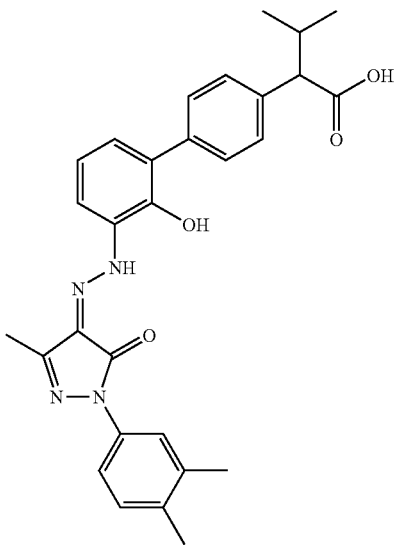

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-3-methyl-butyric acid (Compound 112) was prepared as in Scheme I. $^1$H NMR (500 MHz, DMSO-d$_6$) δ 13.74 (s, 1H), 12.33 (s, 1H), 9.59 (s, 1H), 7.71 (d, J=2.0 Hz, 1H), 7.68 (dd, J=7.6, 2.3 Hz, 1H), 7.63 (dd, J=8.3, 2.0 Hz, 1H), 7.54 (d, J=8.1 Hz, 2H), 7.42 (d, J=8.1 Hz, 2H), 7.20 (d, J=8.3 Hz, 1H), 7.14 (dd, J=7.6, 2.3 Hz, 1H), 7.11 (t, J=7.6 Hz, 1H), 3.17 (d, J=10.5 Hz, 1H), 2.33 (s, 3H), 2.27 (s, 3H), 2.23 (s, 3H), 1.06 (m, 1H), 1.04 (d, J=6.6 Hz, 3H), 0.72 (d, J=6.6 Hz, 3H).

Example 13

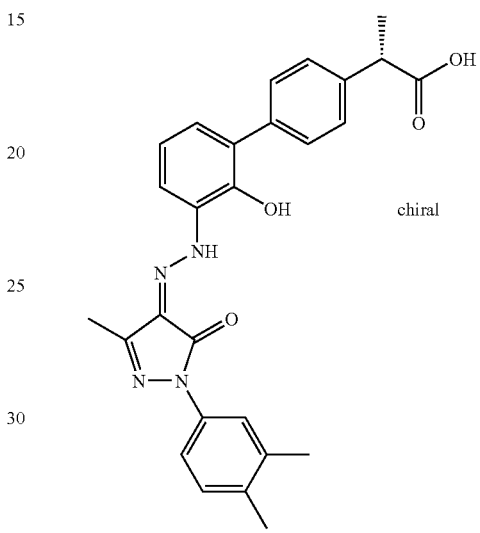

(−)-2-(S)-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionic acid (Compound 113) was prepared as in Scheme I. $^1$H NMR (500 MHz, DMSO-d$_6$) δ 13.73 (m, 1H), 12.37 (s, 1H), 9.60 (s, 1H), 7.71 (d, J=2.2 Hz, 1H), 7.67 (dd, J=6.2, 3.5 Hz, 1H), 7.63 (dd, J=8.2, 2.2 Hz, 1H), 7.54 (d, J=8.3 Hz, 2H), 7.40 (d, J=8.3 Hz, 2H), 7.20 (d, J=8.2 Hz, 1H), 7.13-7.09 (m, 2H), 3.74 (q, J=7.1 Hz, 1H), 2.32 (s, 3H), 2.27 (s, 3H), 2.22 (s, 3H), 1.41 (d, J=7.1 Hz, 3H).

Example 14

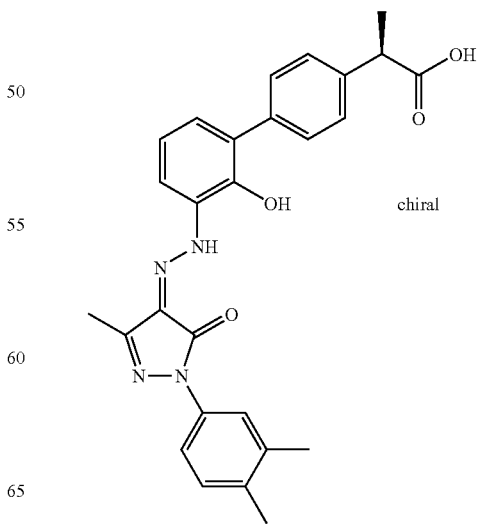

(+)-2-(R)-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionic acid (Compound 114) was prepared as in Scheme I. $^1$H NMR (500 MHz, DMSO-d$_6$) δ 13.73 (s, 1H), 12.37 (s, 1H), 9.61 (s, 1H), 7.71 (d, J=2.0 Hz, 1H), 7.68 (dd, J=6.1, 3.4 Hz, 1H), 7.63 (dd, J=8.2, 2.0 Hz, 1H), 7.54 (d, J=8.1 Hz, 2H), 7.41 (d, J=8.1 Hz, 2H), 7.20 (d, J=8.2 Hz, 1H), 7.14-7.10 (m, 2H), 3.74 (q, J=7.2 Hz, 1H), 2.33 (s, 3H), 2.27 (s, 3H), 2.23 (s, 3H), 1.41 (d, J=7.2 Hz, 3H).

Example 15

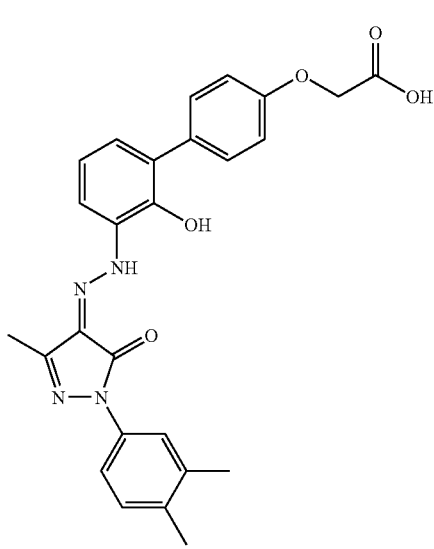

(3'-{N'-[1-(3,4-Dimethyl-phenyl)-3-methyl-5-oxo-1,5-dihydro-pyrazol-4-ylidene]-hydrazino}-2'-hydroxy-biphenyl-4-yloxy)-acetic acid (Compound 115) was prepared as in Scheme I. $^1$H NMR (500 MHz, DMSO-d$_6$) δ 7.71 (m, 1H), 7.65-7.62 (m, 2H), 7.49 (d, J=8.4 Hz, 2H), 7.19 (d, J=8.3 Hz, 1H), 7.10-7.07 (m, 2H), 7.00 (d, J=8.4 Hz, 2H), 4.69 (s, 2H), 2.32 (s, 3H), 2.26 (s, 3H), 2.22 (s, 3H).

Example 16

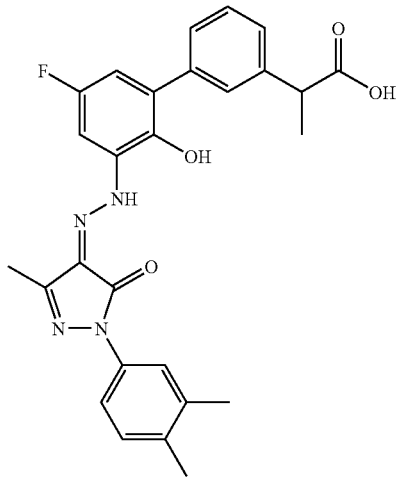

(±)-2-(3'-{N'-[1-(3,4-Dimethyl-phenyl)-3-methyl-5-oxo-1,5-dihydro-pyrazol-4-ylidene]-hydrazino}-5'-fluoro-2'-hydroxy-biphenyl-3-yl)-propionic acid (Compound 116) was prepared as in Scheme I. $^1$H NMR (500 MHz, DMSO-d$_6$) δ 13.63 (s, 1H), 12.37 (s, 1H), 9.53 (s, 1H), 7.70 (d, J=2.2 Hz, 1H), 7.62 (dd, J=8.3, 2.2 Hz, 1H), 7.54 (t, J=1.4 Hz, 1H), 7.50 (dt, J=7.6, 1.4 Hz, 1H), 7.45 (dd, J=9.2, 3.2 Hz, 1H), 7.45 (t, J=7.6 Hz, 1H), 7.34 (dt, J=7.6, 1.4 Hz, 1H), 7.21 (d, J=8.3 Hz, 1H), 6.97 (dd, J=9.3, 3.2 Hz, 1H), 3.76 (q, J=7.1 Hz, 1H), 2.33 (s, 3H), 2.27 (s, 3H), 2.23 (s, 3H), 1.42 (d, J=7.1 Hz, 3H).

Example 17

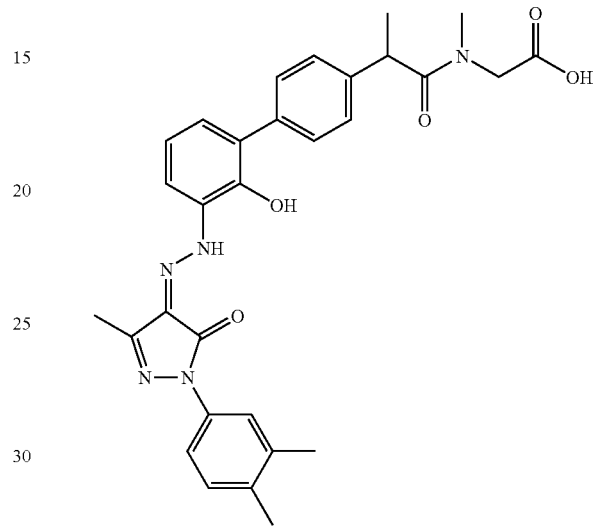

(±)-{[2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionyl]-methyl-amino}acetic acid (Compound 117) was prepared as in Scheme I. $^1$H NMR (500 MHz, DMSO-d$_6$) δ 7.81-7.74 (m, 4H), 7.42 (dd, J=7.9, 1.5 Hz, 1H), 7.24 (d, J=7.9 Hz, 1H), 7.15 (d, J=7.9 Hz, 1H), 7.11 (d, J=7.9 Hz, 1H), 7.04 (m, 1H), 6.29 (t, J=7.9 Hz, 1H), 4.07-3.63 (m, 3H), 2.93 (s, 3H, A), 2.80 (s, 3H, B), 2.31 (s, 3H), 2.23 (s, 3H), 2.20 (s, 3H), 1.29 (d, J=6.6 Hz, 3H, A), 1.27 (d, J=6.8 Hz, 3H, B)

Example 18

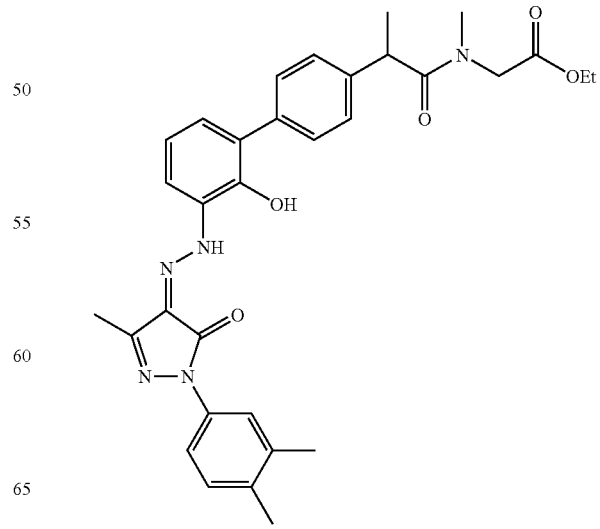

(±)-{[2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionyl]-methyl-amino}-acetic acid ethyl ester (Compound 118) was prepared as in Scheme I. $^1$H NMR (500 MHz, DMSO-d$_6$) δ 13.74 (s, 1H), 9.58 (s, 1H), 7.71 (d, J=2.1 Hz, 1H), 7.67 (m, 1H), 7.63 (dd, J=8.2, 2.1 Hz, 1H), 7.54 (d, J=8.3 Hz, 2H, A), 7.51 (d, J=8.3 Hz, 2H, B), 7.40 (d, J=8.3 Hz, 2H, A), 7.38 (d, J=8.3 Hz, 2H, B), 7.20 (d, J=8.2 Hz, 1H), 7.14-7.10 (m, 2H), 4.21 (q, J=6.8 Hz, 1H), 4.10 (q, J=7.1 Hz, 2H), 4.09 (m, 2H), 3.00 (s, 3H, A), 2.84 (s, 3H, B), 2.32 (s, 3H), 2.27 (s, 3H), 2.23 (s, 3H), 1.33 (d, J=6.8 Hz, 3H, A), 1.33 (d, J=6.8 Hz, 3H, B), 1.18 (t, J=7.1 Hz, 3H, A), 1.17 (t, J=7.1 Hz, 3H, B). (Mixture of two amide isomers A/B ~75:25.)

Example 19

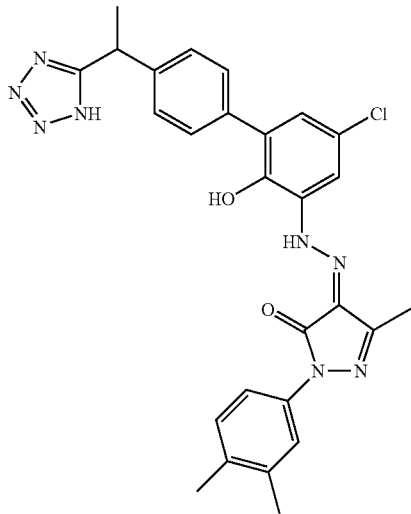

(±)-4-({5-Chloro-2-hydroxy-4'-[1-(1H-tetrazol-5-yl)-ethyl]-biphenyl-3-yl}-hydrazono)-2-(3,4-dimethyl-phenyl)-5-methyl-2,4-dihydro-pyrazol-3-one (Compound 119) was prepared as described in Scheme I. $^1$H NMR (500 MHz, Acetone-d$_6$) δ 7.77 (m, 1H), 7.72 (d, J=2.5 Hz, 1H), 7.71 (m, 1H), 7.51 (d, J=8.0 Hz, 2H), 7.43 (d, J=8.0 Hz, 2H), 7.17 (d, J=8.2 Hz, 1H), 7.06 (d, J=2.5 Hz, 1H), 4.67 (q, J=7.3 Hz, 1H), 2.36 (s, 3H), 2.29 (s, 3H), 2.24 (s, 3H), 1.81 (d, J=7.3 Hz, 3H).

Example 20

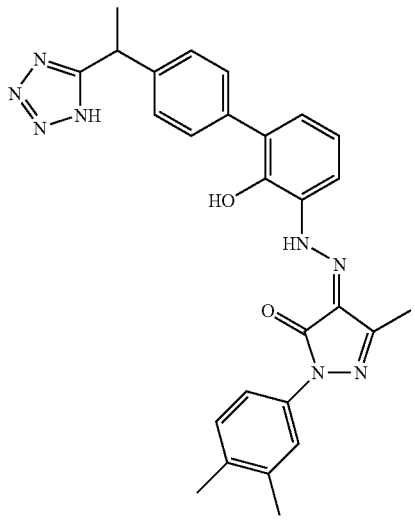

(±)-2-(3,4-Dimethyl-phenyl)-4-({2-hydroxy-4'-[-(1H-tetrazol-5-yl)-ethyl]-biphenyl-3-yl}-hydrazono)-5-methyl-2,4-dihydro-pyrazol-3-one (Compound 120) was prepared as described in Scheme I. $^1$H NMR (500 MHz, Acetone-d$_6$) δ 7.79 (d, J=2.0 Hz, 1H), 7.76 (dd, J=7.6, 2.0 Hz, 1H), 7.72 (dd, J=8.2, 2.0 Hz, 1H), 7.51 (d, J=8.0 Hz, 2H), 7.43 (d, J=8.0 Hz, 2H), 7.17 (d, J=8.2 Hz, 1H), 7.12 (t, J=7.6 Hz, 1H), 7.09 (dd, J=7.6, 2.0 Hz, 1H), 4.68 (q, J=6.9 Hz, 1H), 2.35 (s, 3H), 2.29 (s, 3H), 2.25 (s, 3H), 1.82 (d, J=6.9 Hz, 3H).

Example 21

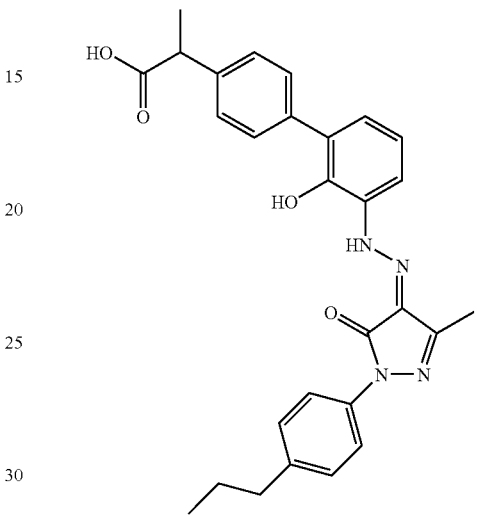

(±)-2-(2'-Hydroxy-3'-{N'-[3-methyl-5-oxo-1-(4-propyl-phenyl)-1,5-dihydro-pyrazol-4-ylidene]-hydrazino}-biphenyl-4-yl)-propionic acid (Compound 121) was prepared as described in Scheme I. $^1$H NMR (500 MHz, Acetone-d$_6$) δ 7.92 (d, J=8.6 Hz, 2H), 7.77 (m, 1H), 7.51 (d, J=8.3 Hz, 2H), 7.44 (d, J=8.3 Hz, 2H), 7.27 (d, J=8.6 Hz, 2H), 7.15-7.10 (m, 2H), 2.60 (t, J=7.3 Hz, 2H), 2.36 (s, 3H), 2.27 (q, J=7.2 Hz, 1H), 1.64 (m, 2H), 1.49 (d, J=7.2 Hz, 3H), 0.93 (t, J=7.3 Hz, 3H).

Example 22

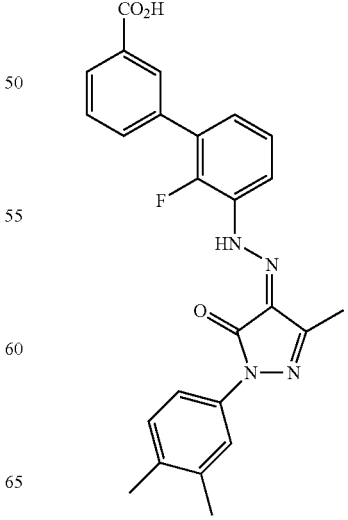

3'-{N'-[1-(3,4-Dimethyl-phenyl)-3-methyl-5-oxo-1,5-dihydro-pyrazol-4-ylidene]-hydrazino}-2'-fluoro-biphenyl-3-carboxylic acid (Compound 122) was prepared as in Scheme III. 1H NMR (500 MHz, Acetone-$d_6$) δ 8.17 (t, J=1.7 Hz, 1H), 8.10 (ddd, J=7.7, 1.7, 1.2 Hz, 1H), 7.81 (ddd, J=7.7, 1.7, 1.2 Hz, 1H), 7.72 (m, 1H), 7.67 (t, J=7.7 Hz, 1H), 7.62 (d, J=1.9 Hz, 1H), 7.58 (m, 1H), 7.57 (m, 1H), 7.52 (m, 1H), 7.40 (m, 1H), 7.19 (d, J=8.2 Hz, 1H), 2.29 (s, 3H), 2.25 (s, 3H), 2.13 (s, 3H).

Example 23

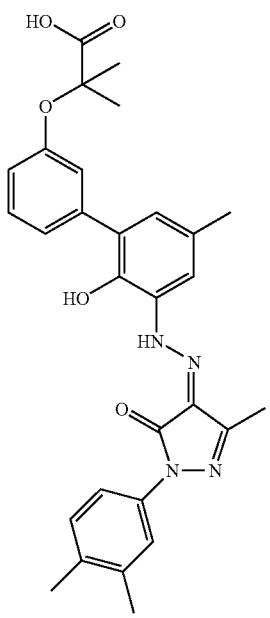

2-(3'-{N'-[1-(3,4-Dimethyl-phenyl)-3-methyl-5-oxo-1,5-dihydro-pyrazol-4-ylidene]-hydrazino}-2'-hydroxy-5'-methyl-biphenyl-3-yloxy)-2-methyl-propionic acid (Compound 123) was prepared as in Scheme I. $^1$H NMR (500 MHz, Acetone-$d_6$) δ 13.86 (s, 1H), 7.80 (d, J=1.7 Hz, 1H), 7.73 (dd, J=8.2, 1.9 Hz, 1H), 7.58 (d, J=1.4 Hz, 1H), 7.35 (t, J=7.9 Hz, 1H), 7.17 (d, J=8.2 Hz, 1H), 7.14 (d, J=7.9 Hz, 1H), 7.07 (m, 1H), 6.96-6.90 (m, 2H), 2.36 (s, 3H), 2.34 (s, 3H), 2.29 (s, 3H), 2.25 (s, 3H), 1.62 (s, 6H)

Example 24

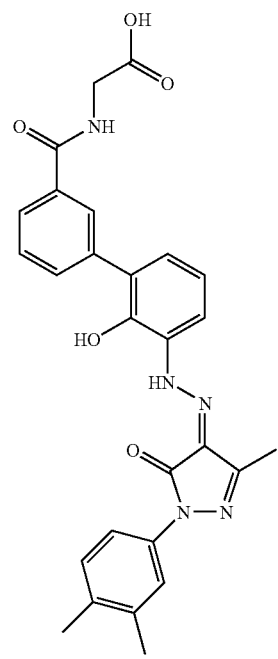

[(3'-{N'-[1-(3,4-Dimethyl-phenyl)-3-methyl-5-oxo-1,5-dihydro-pyrazol-4-ylidene]-hydrazino}-2'-hydroxy-biphenyl-3-carbonyl)-amino]-acetic acid (Compound 124) was prepared as in Scheme I. $^1$H NMR (500 MHz, Acetone-$d_6$) δ 13.87 (s, 1H), 8.20 (m,1H), 8.04 (s, 1H), 7.94 (d, J=7.6 Hz, 1H), 7.80-7.76 (m, 2H), 7.74-7.67 (m, 2H), 7.58 (t, J=7.6 Hz, 1H), 7.18-7.11 (m, 3H), 4.17 (d, J=5.6 Hz, 2H), 3.62 (m, 1H), 2.34 (s, 3H), 2.28 (s, 3H), 2.23 (s, 3H)

Example 25

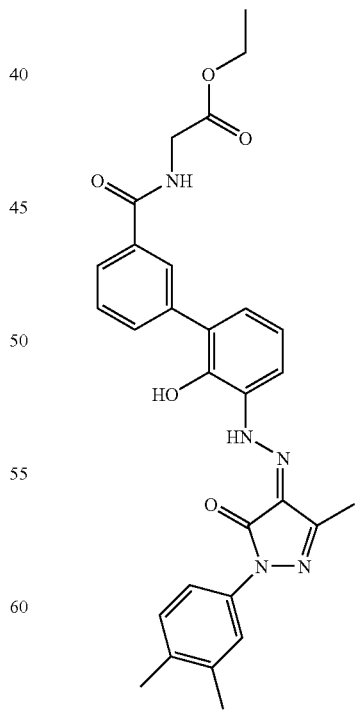

[(3'-{N'-[1-(3,4-Dimethyl-phenyl)-3-methyl-5-oxo-1,5-dihydro-pyrazol-4-ylidene]-hydrazino}-2'-hydroxy-biphenyl-3-carbonyl)-amino]-acetic acid ethyl ester (Compound 125) was prepared as in Scheme I. ¹H NMR (500 MHz, CDCl₃) δ 13.88 (s, 1H), 8.12 (s, 1H), 7.97 (t, J=1.7 Hz, 1H), 7.82 (ddd, J=7.7, 1.7, 1.1 Hz, 1H), 7.69 (d, J=2.2 Hz, 1H), 7.67 (ddd, J=7.7, 1.7, 1.1 Hz, 1H), 7.64 (dd, J=8.2, 2.2 Hz, 1H), 7.54 (t, J=7.7 Hz, 1H), 7.39 (dd, J=7.9, 1.6 Hz, 1H), 7.16 (d, J=8.2 Hz, 1H), 7.10 (dd, J=7.9, 1.6 Hz, 1H), 7.04 (t, J=7.9 Hz, 1H), 6.85 (t, J=5.0 Hz, 1H), 4.24 (q, J=7.1 Hz, 2H), 4.23 (d, J=5.0 Hz, 2H), 2.34 (s, 3H), 2.30 (s, 3H), 2.26 (s, 3H), 1.31 (t, J=7.1 Hz, 3H)

Example 26

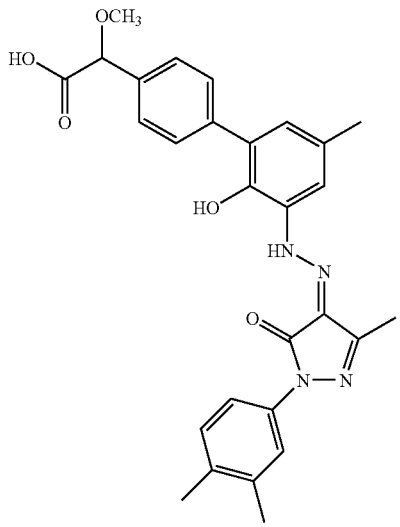

(±)-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-methoxy-acetic acid (Compound 126) was prepared as in Scheme I. ¹H NMR (500 MHz, Acetone-d₆) δ 13.69 (s, 1H), 7.72 (d, J=1.8 Hz, 1H), 7.65 (dd, J=8.2, 2.1 Hz, 1H), 7.55-7.49 (m, 5H), 7.18 (d, J=8.2 Hz, 1H), 6.92 (d, J=1.8 Hz, 1H), 4.87 (s, 1H), 3.42 (s, 3H), 2.34 (s, 3H), 2.32 (s, 3H), 2.29 (s, 3H), 2.25 (s, 3H).

Example 27

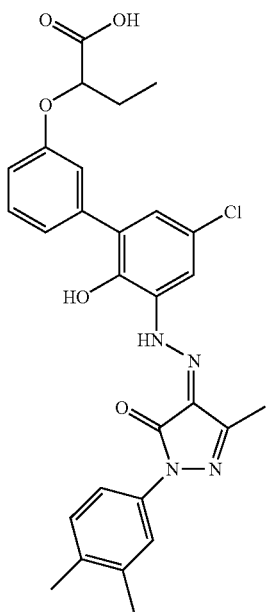

(±)-2-(5'-Chloro-3'-{N'-[1-(3,4-dimethyl-phenyl)-3-methyl-5-oxo-1,5-dihydro-pyrazol-4-ylidene]-hydrazino}-2'-hydroxy-biphenyl-3-yloxy)-butyric acid (Compound 127) was prepared as in Scheme I. ¹H NMR (500 MHz, Methanol-d₄) δ 7.64 (d, J=2.1 Hz, 1H), 7.58 (d, J=2.5 Hz, 1H), 7.56 (dd, J=8.2, 2.1 Hz, 1H), 7.36 (dd, J=8.3, 7.6 Hz, 1H), 7.12 (d, J=8.2 Hz, 1H), 7.05 (ddd, J=7.6, 1.5, 0.8 Hz, 1H), 7.03 (dd, J=2.5, 1.5 Hz, 1H), 7.00 (d, J=2.5 Hz, 1H), 6.94 (ddd, J=8.3, 2.5, 0.8 Hz, 1H), 4.57 (dd, J=7.4, 4.9 Hz, 1H), 2.33 (s, 3H), 2.27 (s, 3H), 2.23 (s, 3H), 1.97 (m, 2H), 1.10 (t, J=7.4 Hz, 3H).

Example 28

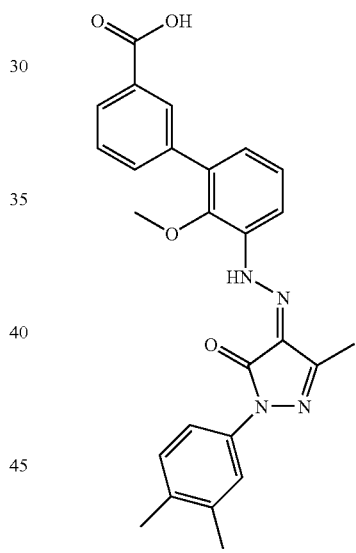

3'-{N'-[1-(3,4-Dimethyl-phenyl)-3-methyl-5-oxo-1,5-dihydro-pyrazol-4-ylidene]-hydrazino}-2'-methoxy-biphenyl-3-carboxylic acid (Compound 128) was prepared as in Scheme I. ¹H NMR (500 MHz, Acetone-d₆) δ 8.33 (t, J=1.6 Hz, 1H), 8.12 (ddd, J=7.8, 1.6, 1.1 Hz, 1H), 7.93 (ddd, J=7.8, 1.6, 1.1 Hz, 1H), 7.86 (dd, J=7.9, 1.6 Hz, 1H), 7.80 (d, J=2.1 Hz, 1H), 7.74 (dd, J=8.3, 2.1 Hz, 1H), 7.67 (t, J=7.8 Hz, 1H), 7.40 (t, J=7.9 Hz, 1H), 7.31 (dd, J=7.9, 1.6 Hz, 1H), 7.21 (d, J=8.3 Hz, 1H), 3.57 (s, 3H), 2.37 (s, 3H), 2.31 (s, 3H), 2.27 (s, 3H).

Example 29

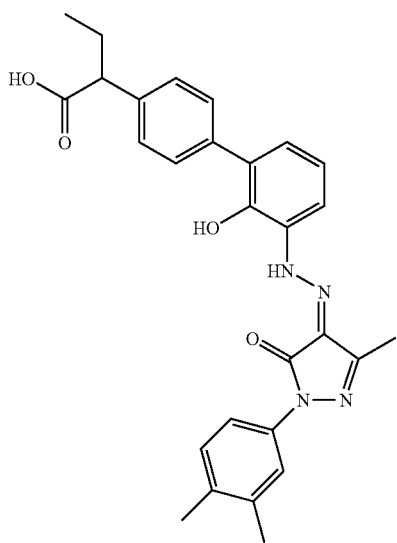

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-butyric acid (Compound 129) was prepared as described in Scheme I. $^1$H NMR (500 MHz, DMSO-d$_6$) δ 13.73 (s, 1H), 12.37 (s, 1H), 9.60 (s, 1H), 7.71 (d, J=1.8 Hz, 1H), 7.67 (dd, J=7.0, 2.6 Hz, 1H), 7.63 (dd, J=8.2, 1.8 Hz, 1H), 7.54 (d, J=8.0 Hz, 2H), 7.40 (d, J=8.0 Hz, 2H), 7.20 (d, J=8.2 Hz, 1H), 7.14-7.09 (m, 2H), 3.48 (t, J=7.3 Hz, 1H), 2.32 (s, 3H), 2.27 (s, 3H), 2.22 (s, 3H), 2.01 (qn, J=7.3 Hz, 1H), 1.70 (qn, J=7.3 Hz, 1H), 0.88 (t, J=7.3 Hz, 3H).

Example 30

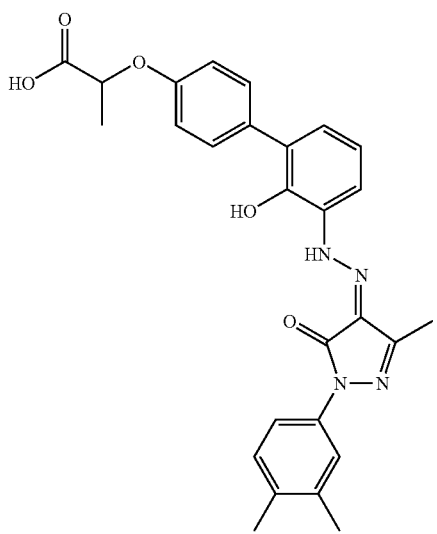

(±)-2-(3'-{N'-[-(3,4-Dimethyl-phenyl)-3-methyl-5-oxo-1,5-dihydro-pyrazol-4-ylidene]-hydrazino}-2'-hydroxy-biphenyl-4-yloxy)-propionic acid (Compound 130) was prepared as described in Scheme I. $^1$H NMR (500 MHz, DMSO-d$_6$) 7.72 (s, 1H), 7.64 (m, 1H), 7.49 (m, 2H), 7.19 (m, 1H), 7.05 (m, 2H), 6.96 (m, 2H), 6.87 (m, 1H), 4.84 (m, 1H), 2.32 (s, 3H), 2.27 (s, 3H), 2.22 (s, 3H), 1.53 (d, J=6.8 Hz, 3H).

Example 31

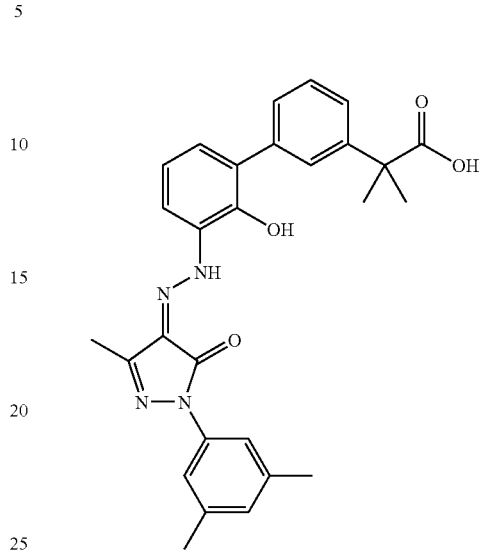

2-(5'-Chloro-3'-{N'-[1-(3,5-dimethyl-phenyl)-3-methyl-5-oxo-1,5-dihydro-pyrazol-4-ylidene]-hydrazino}-2'-hydroxy-biphenyl-3-yl)-2-methyl-propionic acid (Compound 131) was prepared as described in Scheme I. $^1$H NMR (500 MHz, DMSO-d$_6$) 13.78 (s, 1H), 12.40 (s, 1H), 9.62 (s, 1H), 7.69 (m, 1H), 7.58 (s, 2H), 7.55 (s, 1H), 7.48-7.43 (m, 2H), 7.37 (m, 1H), 7.16-7.12 (m, 2H), 6.87 (s, 1H), 2.33 (s, 3H), 2.32 (s, 6H), and 1.53 (s, 6H).

What is claimed is:

1. A compound selected from the group consisting of:
   (±)-2-(3'-{N'-[1-(3,4-Dimethylphenyl)-3-methyl-5-oxo-1,5-dihydro-pyrazol-4-ylidene]-hydrazino}-2'-hydroxy-biphenyl-3-yl)-propionic acid (Compound 101);
   2-(5'-Chloro-3'-{N'-[1-(3,4-dimethyl-phenyl)-3-methyl-5-oxo-1,5-dihydro-pyrazol-4-ylidene]-hydrazino}-2'-hydroxy-biphenyl-3-yl)-2-methyl-propionic acid (Compound 102);
   (±)-2-(3'-{N'-[1-(3,4-Dimethylphenyl)-3-methyl-5-oxo-1,5-dihydro-pyrazol-4-ylidene]-hydrazino}-2'-hydroxy-biphenyl-3-yl)-3-phenylpropionic acid (Compound 103);
   (±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-3-yl)-butyric acid (Compound 104);
   (±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionic acid (Compound 105);
   (±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-thiopropionic acid (Compound 106);
   (±)-2-(3'-{N'-[1-(3,4-Dimethyl-phenyl)-3-methyl-5-oxo-1,5-dihydro-pyrazol-4-ylidene]-hydrazino}-5'-fluoro-2'-hydroxy-biphenyl-4-yl)-propionic acid (Compound 107);
   3-{N'-[1-(3,4-Dimethyl-phenyl)-3-methyl-5-oxo-1,5-dihydro-pyrazol-4-ylidene]-hydrazino}-biphenyl-2,3'-dicarboxylic acid (Compound 108);

(±)-2-(3'-{N'-[1-(3,4-Dimethyl-phenyl)-3-methyl-5-oxo-1,5-dihydro-pyrazol-4-ylidene]-hydrazino}-2'-hydroxy-5'-methyl-biphenyl-4-yl)-propionic acid (Compound 109);

2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-2-methyl-propionic acid (Compound 110);

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-hexanoic acid (Compound 111);

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-3-methyl-butyric acid (Compound 112);

(−)-2-(S)-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionic acid (Compound 113);

(+)-2-(R)-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionic acid (Compound 114);

(3'-{N'-[1-(3,4-Dimethyl-phenyl)-3-methyl-5-oxo-1,5-dihydro-pyrazol-4-ylidene]-hydrazino}-2'-hydroxy-biphenyl-4-yloxy)-acetic acid (Compound 115);

(±)-2-(3'-{N'-[1-(3,4-Dimethyl-phenyl)-3-methyl-5-oxo-1,5-dihydro-pyrazol-4-ylidene]-hydrazino}-5'-fluoro-2'-hydroxy-biphenyl-3-yl)-propionic acid (Compound 116);

(±)-{[2-(3'-{N'-[1-(3,4-Dimethyl-phenyl)-3-methyl-5-oxo-1,5-dihydro-pyrazol-4-ylidene]- hydrazino}-2'-hydroxy-biphenyl-4-yl)-propionyl]-methyl-amino} acetic acid (Compound 117);

(±)-{[2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-propionyl]-methyl-amino}-acetic acid ethyl ester (Compound 118);

(±)-4-({5-Chloro-2-hydroxy-4'-[1-(1H-tetrazol-5-yl)-ethyl]-biphenyl-3-yl}-hydrazono)-2-(3,4-dimethyl-phenyl)-5-methyl-2,4-dihydro-pyrazol-3-one (Compound 119);

(±)-2-(3,4-Dimethyl-phenyl)-4-({2-hydroxy-4'-[1-(1H-tetrazol-5-yl)-ethyl]-biphenyl-3-yl}-hydrazono)-5-methyl-2,4-dihydro-pyrazol-3-one (Compound 120);

(±)-2-(2'-Hydroxy-3'-{N'-[3-methyl-5-oxo-1-(4-propyl-phenyl)-1,5-dihydro-pyrazol-4-ylidene]-hydrazino}-biphenyl-4-yl)-propionic acid (Compound 121);

3-{N'-[1-(3,4-Dimethyl-phenyl)-3-methyl-5-oxo-1,5-dihydro-pyrazol-4-ylidene]-hydrazino}-2'-fluoro-biphenyl-3-carboxylic acid (Compound 122);

2-(3'-{N'-[1-(3,4-Dimethyl-phenyl)-3-methyl-5-oxo-1,5-dihydro-pyrazol-4-ylidene]-hydrazino}-2'-hydroxy-5'-methyl-biphenyl-3-yloxy)-2-methyl-propionic acid (Compound 123);

[(3'-{N'-[1-(3,4-Dimethyl-phenyl)-3-methyl-5-oxo-1,5-dihydro-pyrazol-4-ylidene]-hydrazino}-2'-hydroxy-biphenyl-3-carbonyl)-amino]-acetic acid (Compound 124);

[(3'-{N'-[1-(3,4-Dimethyl-phenyl)-3-methyl-5-oxo-1,5-dihydro-pyrazol-4-ylidene]-hydrazino}-2'-hydroxy-biphenyl-3-carbonyl)-amino]-acetic acid ethyl ester (Compound 125);

(±)-(3'-{N'-[1-(3,4-Dimethyl-phenyl)-3-methyl-5-oxo -1,5-dihydro-pyrazol-4-ylidene]-hydrazino}-2'-hydroxy-biphenyl-4-yl)-methoxy-acetic acid (Compound 126);

(±)-2-(5'-Chloro-3'-{N'-[1-(3,4-dimethyl-phenyl)-3-methyl-5-oxo-1,5-dihydro-pyrazol-4-ylidene]-hydrazino}-2'-hydroxy-biphenyl-3-yloxy)-butyric acid (Compound 127);

3'-{N'-[1-(3,4-Dimethyl-phenyl)-3-methyl-5-oxo-1,5-dihydro-pyrazol-4-ylidene]-hydrazino}-2'-methoxy-biphenyl-3-carboxylic acid (Compound 128);

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yl)-butyric acid (Compound 129);

(±)-2-(3'-{N'-[1-(3,4-Dimethyl-phenyl)-3-methyl-5-oxo-1,5-dihydro-pyrazol-4-ylidene]-hydrazino}-2'-hydroxy-biphenyl-4-yloxy)-propionic acid (Compound 130);

2-(5'-Chloro-3'-{N'-[1-(3,5-dimethyl-phenyl)-3-methyl-5-oxo-1,5-dihydro-pyrazol-4-ylidene]-hydrazino}-2'-hydroxy-biphenyl-3-yl)-2-methyl-propionic acid (Compound 131);

or a pharmaceutically acceptable salt, ester, amide, or prodrug thereof.

2. A method of treating thrombocytopenia in a patient suffering therefrom comprising administering to the patient a compound of claim 1.

3. The method of claim 2 wherein the thrombocytopenia results from radiation or chemotherapy.

4. The method of claim 2 further comprising harvesting cells from the patient.

5. The method of claim 2 wherein the patient also suffers from a disease selected from amyotrophic lateral sclerosis, multiple sclerosis, and multiple dystrophy.

6. The method of claim 2 wherein the patient suffers from injury to the spinal cord.

7. A pharmaceutical composition comprising
i) a physiologically acceptable carrier, diluent, or excipient, or a combination thereof; and
ii) a compound of claim 1.

* * * * *